(12) United States Patent
Febbraio et al.

(10) Patent No.: US 9,765,129 B2
(45) Date of Patent: Sep. 19, 2017

(54) TREATMENT OF OBESITY

(71) Applicants: Baker Medical Research Institute, Melbourne (AU); Christian-Albrechts-Universität zu Kiel, Kiel (DE)

(72) Inventors: Mark Anthony Febbraio, Lower Plenty (AU); Stefan Rose-John, Schellhorn (DE)

(73) Assignees: Baker Medical Research Institute, Melbourne (AU); Christian-Albrechts-Universität zu Kiel, Kiel (DE)

( * ) Notice: Subject to any disclaimer, the term of this patent is extended or adjusted under 35 U.S.C. 154(b) by 0 days.

(21) Appl. No.: 13/968,977

(22) Filed: Aug. 16, 2013

(65) Prior Publication Data
US 2014/0140949 A1  May 22, 2014

Related U.S. Application Data

(62) Division of application No. 12/593,708, filed as application No. PCT/AU2008/000438 on Mar. 28, 2008, now abandoned.

(60) Provisional application No. 60/920,822, filed on Mar. 30, 2007.

(51) Int. Cl.
| | |
|---|---|
| *A61K 38/20* | (2006.01) |
| *C07K 14/54* | (2006.01) |
| *C07K 14/475* | (2006.01) |
| *C07K 14/48* | (2006.01) |
| *A61K 38/00* | (2006.01) |

(52) U.S. Cl.
CPC ........ *C07K 14/5412* (2013.01); *C07K 14/475* (2013.01); *C07K 14/48* (2013.01); *A61K 38/00* (2013.01); *C07K 2319/00* (2013.01)

(58) Field of Classification Search
None
See application file for complete search history.

(56) References Cited

FOREIGN PATENT DOCUMENTS

JP   2001000189 A2 *  1/2001

OTHER PUBLICATIONS

Watt et al., Nature Medicine, 12(5):541-548, May 2006.*
Kallen et al., Journal of Biological Chemistry, 274(17):11859-11867, 1999.*
Schuster et al., Journal of Biological Chemistry, 278(11):9528-9535, 2003.*
Febbraio, Journal of Clinical Investigation, 117(4):841-849, 2007.*
Matthews et al., J Mol Med, 86:353-361, Jan. 22, 2008.*
Elson et al., 2000. *Nat. Neurosci.* 3:867-872.
Florholmen et al., 2006. *Diabetologia* 49:724-731.
Zvonic et al., 2004. *J. Biol. Chem.* 279(46):47572-47579.
Carey, et al., (2006, Diabetes, 55: 2688-2697).

* cited by examiner

*Primary Examiner* — Marianne P Allen
(74) *Attorney, Agent, or Firm* — Knobbe Martens Olson & Bear LLP

(57) ABSTRACT

The present invention relates generally to a method of increasing lipid oxidation in a mammal and to agents useful for same. More particularly, the present invention relates to a method of increasing lipid oxidation in a mammal by administering a ligand which interacts with the IL-6 receptor and signals via interaction with a gp130/LIF receptor heterodimer. In a related aspect, the present invention provides a method of increasing insulin sensitivity in a mammal. The method of present invention is useful, inter alia, in the treatment and/or prophylaxis of conditions characterized by unwanted lipid accumulation (such as obesity, obesity induced-metabolic disorders, type II diabetes, dyslipidemia, glucose intolerance, insulin resistance, obstructive sleep apnea, cardiovascular disease or non-alcoholic fatty liver disease) or inadequate insulin sensitivity.

3 Claims, 9 Drawing Sheets

Red Gastrocnemius

Soleus

Liver

Epididymal Adipose Tissue

TREATMENT OF OBESITY

CROSS REFERENCE TO RELATED APPLICATIONS

This application is a divisional of and claims the benefit and priority to U.S. patent application Ser. No. 12/593,708, filed on Mar. 30, 2010, which is a U.S. National Phase application of PCT International Application Number PCT/AU2008/000438, filed on Mar. 28, 2008, designating the United States of America and published in the English language, which is an International Application of and claims the benefit of priority to U.S. Provisional Application No. 60/920,822, filed on Mar. 30, 2007. The disclosures of the above-referenced applications are hereby expressly incorporated by reference in their entireties.

REFERENCE TO SEQUENCE LISTING

The present application is being filed along with a sequence listing in electronic format. The sequence listing is provided as a file entitled Sequencelisting.txt, created Aug. 16, 2013 which is 9 KB in size. The information in the electronic format of the sequence listing is incorporated herein by reference in its entirety.

FIELD OF THE INVENTION

The present invention relates generally to a method of increasing lipid oxidation in a mammal and to agents useful for same. More particularly, the present invention relates to a method of increasing lipid oxidation in a mammal by administering a ligand which interacts with the IL-6 receptor and signals via interaction with a gp130/LIF receptor heterodimer. In a related aspect, the present invention provides a method of increasing insulin sensitivity in a mammal. The method of present invention is useful, inter alia, in the treatment and/or prophylaxis of conditions characterised by unwanted lipid accumulation (such as obesity, obesity induced-metabolic disorders, type II diabetes, dyslipidemia, glucose intolerance, insulin resistance, obstructive sleep apnea, cardiovascular disease or non-alcoholic fatty liver disease) or inadequate insulin sensitivity.

BACKGROUND OF THE INVENTION

Bibliographic details of the publications referred to by author in this specification are collected alphabetically at the end of the description.

The reference to any prior art in this specification is not, and should not be taken as, an acknowledgment or any form of suggestion that that prior art forms part of the common general knowledge in Australia.

Obesity is a condition in which the natural energy reserve, stored in the fatty tissue of humans and other mammals, exceeds healthy limits. It is commonly defined as a body mass index (weight divided by height squared) of 30 kg/m$^2$ or higher.

Although obesity is an individual clinical condition, some authorities view it as a serious and growing public health problem, particularly since excessive body weight has been linked to the onset of diseases such as cardiovascular diseases, insulin resistance, dyslipidemia, hypertension, diabetes mellitus type 2 and sleep apnea.

The prevalence of adult obesity has increased approximately 75% in the last quarter century (Flegal, K M et. al., (1999-2000), Prevalence and trends in obesity among US adults, *JAMA* 288:1723-1727). The prevalence of overweight and obese children is also increasing in both developed and developing countries (Mascie-Taylor, C G, and Karim, E, (2003), The burden of chronic disease, *Science* 302:1921-1922). Current therapies to treat obesity centre on lifestyle modifications, but for those individuals who do not respond to such treatment, or cannot adhere to lifestyle intervention programs, bariatric surgery is often used. As this is neither a feasible nor a desirable treatment for a pandemic, drug therapy is a viable intervention for those in whom lifestyle modification has failed. Currently, there are three obesity drugs commonly prescribed. Xenical (orlistat) is a gastrointestinal lipase inhibitor, Sibutramine, a monoamine reuptake inhibitor, and Rimonabant, the first of the endocannabinoid receptor agonists. Disappointingly, none has resulted in consistent and effective weight loss, and to date, all anti-obesity drug trials have been limited by their high attrition rates and lack of long-term morbidity and mortality data (Padwal, R S, and Majumdar, S R (2007) Drug treatment for obesity: orlistat, sibutramine, and rimonbant, *Lancet* 369:71-77). Importantly, these drugs do not act by increasing energy metabolism and, currently, this is the focus of many pharmaceutical approaches.

The discovery of leptin (Zhang, Y et. al. (1994) Positional cloning of the mouse obese gene and its human homologue, *Nature* 372:425-432, Halaas, J L et. al. (1995) Weight-reducing effects of the plasma protein encoded by the obese gene, *Science* 269:543-546) and the leptin receptor (Tartaglia, L A et. al., (1995) Identification and expression cloning of a leptin receptor, OB-R, *Cell* 83:1263-1271), over a decade ago, led to the hope that researchers had at last identified a highly effective molecule and/or pathway that could be targeted in the treatment of obesity. However, it soon became apparent that obesity, in which high circulating concentrations of leptin develop, resulted in leptin resistance whereby endogenous leptin was no longer effective (Van Heek, M et. al. (1997) Diet-induced obese mice develop peripheral, but not central, resistance to leptin, *J. Clin. Invest.* 99:385-390).

Over the past decade a metabolic role for gp130 receptor cytokines has been elucidated. Often termed the "interleukin (IL)-6 family" of cytokines these include IL-6, leukemia inhibitory factor (LIF), IL-11, oncostatin-M, cardiotrophin-1 and ciliary neurotropic factor (CNTF). In particular, CNTF and IL-6 enhance fat oxidation in skeletal muscle and increase insulin sensitivity in vivo, principally via the activation of AMP activated protein kinase (AMPK) in both animals and humans. These results have generated a great deal of excitement as gp130 receptor ligands are now becoming recognised as a potential therapeutic target for obesity-induced insulin resistance. However, despite these major advanced in the understanding of the molecular processes as to how gp130 receptor ligands may enhance insulin sensitivity and act as "anti-obesogenic" agents, clinical trials have not been successful. This has been due principally to two major complications. The first is that IL-6 is pro-inflammatory and while it has positive effects on energy balance and insulin sensitivity when administered acutely, it has negative effects on the progression of many diseases. Secondly, CNTF failed in clinical trials because patients developed antibodies to Axokine®, the human recombinant variant of CNTF (Ettinger, M P, et. al. (2003) Recombinant variant of ciliary neurotrophic factor for weight loss in obese adults: a randomized, dose-ranging study, *JAMA* 289: 1826-1832). This was not entirely surprising since CNTF lacks a secretory signal sequence peptide and, therefore, does not circulate. Still further, due to the low level of CNTF receptors present in the periphery and the lower level of affinity of CNTF for the more light expressed IL-6 receptor, quite high concentration of CNTF were required to be used.

Accordingly, there exists an ongoing need to develop new methods for treating obesity. In work leading up to the present invention it has been determined that in terms of the functioning of IL-6 and CNTF, the unwanted side effects known to be associated with the administration of these molecules can be minimised by activating the IL-6 receptor and facilitating induction of the subsequent signalling via a gp130/LIF receptor heterodimer, rather than the gp130 homodimer which is used by IL-6. The findings of the present invention have now facilitated the development of methodology for increasing lipid oxidation in mammals without the concomittant problems of the induction of an inflammatory state, or the use of high concentrations of cytokine of the generation of autoantibodies. Accordingly, there is now provided a means for therapeutically or prophylactically treating conditions associated with unwanted lipid accumulation.

SUMMARY OF THE INVENTION

Throughout this specification and the claims that follow, unless the context requires otherwise, the word "comprise", or variations such as "comprises" or "comprising" will be understood to imply the inclusion of a stated element or integer or group of elements or integers, but not the exclusion of any other element or integer or group of elements or integers.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

Unless otherwise defined, all technical and scientific terms used herein have the same meaning as commonly understood by one of ordinary skill in the art to which this invention belongs.

The subject specification contains amino acid sequence information prepared using the programme PatentIn Version 3.1, presented herein after the bibliography. Each amino acid sequence is identified in the sequence listing by the numeric indicator <210> followed by the sequence identifier (eg. <210>1, <210>2, etc). The length, type of sequence (amino acid, etc.) and source organism for each sequence is indicated by information provided in the numeric indicator fields <211>m <212> and <213>, respectively. Amino acid sequences referred to in the specification are identified by the indicator SEQ ID NO: followed by the sequence identifier (eg. SEQ ID NO:1, SEQ ID NO: 2, etc). The sequence identifier referred to in the specification correlates to the information provided in numeric indicator field <400> in the sequence listing, which is followed by the sequence identifier (eg. <400>1, <400>2, etc). That is SEQ ID NO: 1 as detailed in the specification correlates to the sequence indicated as <400>1 in the sequence listing.

One aspect of the present invention is directed to a method of inducing lipid oxidation in a mammal, said method comprising administering to said mammal a ligand which binds to the IL-6 receptor and signals via a gp130/LIF receptor heterodimer.

In another aspect the present invention is directed to a method of inducing lipid oxidation in a mammal, said method comprising administering to said mammal a ligand which binds to the IL-6 receptor and signals via a gp130/LIF receptor heterodimer wherein the IL-6 receptor binding site of said ligand has a greater affinity for the IL-6 receptor than the CNTF receptor.

In yet another aspect the present invention is directed to a method of inducing lipid oxidation in a mammal, said method comprising administering to said mammal a ligand comprising an IL-6 receptor binding site, a gp130 binding site and a LIF receptor binding site.

In still another aspect the present invention provides a method of inducing lipid oxidation in a mammal, said method comprising administering to said mammal a ligand comprising a binding site substantially similar to the IL-6R binding site of IL-6, a gp130 binding site and a LIF receptor binding site.

In a further aspect there is provided a method of inducing lipid oxidation in a mammal, said method comprising administering to said mammal a ligand comprising a binding site substantially similar to the IL-6R binding site of IL-6, a binding site substantially similar to the gp130 binding site of IL-6 and a binding site substantially similar to the LIF receptor binding site of CNTF.

In yet another aspect, said ligand comprises sites I and II of IL-6, or substantially similar sites as hereinbefore defined and site III of CNTF or substantially similar site.

In yet still another aspect, the subject ligand is an IL-6/CNTF chimeric protein. More specifically, an exemplary chimera is one in which the site III loop of CNTF is inserted in IL-6 in place of the site III loop of IL-6. In such chimeras, amino acid residues located in the C-terminal A-helix, the N-terminal AB loop (Glu36-Met56; SEQ ID NO:4) of CNTF may be substituted in place of the IL-6 residues between Arg40-Asn60 (i.e., Arg40 and Asn60 are retained), the C-terminal CD loop with the adjoining N-terminal D helix (Gly147-Leu162; SEQ ID NO:6) of CNTF may be substituted in place of IL-6 residues between Leu151-Arg168 and the BC loop with adjacent parts of B- and C-helix (Leu91-Ile109; SEQ ID NO:5) of CNTF may be substituted in place of the IL-6 residues between Leu101-Arg113.

Preferably, said ligand is IC7, as described in Kallen, K J et. al, (1999) Receptor recognition sites of cytokines are organized as exchangeable moduls: transfer of the LIFR binding site from CNTF to IL-6, *J. Biol. Chem.* 274:11859-11867 or SEQ ID NO: 7 or a substantially similar ligand.

In a further aspect there is provided a method of inducing lipid oxidation in a mammal, said method comprising administering to said mammal IC7, a ligand comprising the SEQ ID NO:7 amino acid sequence or a substantially similar ligand or functional fragment thereof.

In another aspect of the present invention is directed to a method of therapeutically or prophylactically treating a condition in a mammal, which condition is characterised by unwanted lipid accumulation, said method comprising administering to said mammal a ligand which binds to the IL-6 receptor and signals via a gp130/LIF receptor heterodimer.

In still another aspect the present invention is directed to a method of therapeutically or prophylactically treating a condition in a mammal, which condition is characterised by unwanted lipid accumulation, said method comprising administering to said mammal a ligand which binds to the IL-6 receptor and signals via a gp130/LIF receptor heterodimer, wherein the IL-6 receptor binding site of said ligand has a greater affinity for the IL-6 receptor than the CNTF receptor.

In yet still another aspect there is provided a method of therapeutically or prophylactically treating a condition in a mammal, which condition is characterised by unwanted lipid accumulation, said method comprising administering to said mammal a ligand comprising a binding site substantially similar to the IL-6R binding site of IL-6, a binding site substantially similar to the gp130 binding site of IL-6, and a binding site substantially similar to the LIF receptor binding site of CNTF.

In still yet another aspect there is provided a method of therapeutically or prophylactically treating a condition in a mammal, which condition is characterised by unwanted lipid accumulation, said method comprising administering to said mammal IC7, a ligand comprising the SEQ ID NO:7 amino acid sequence or a substantially similar ligand or functional fragment thereof.

Yet another aspect of the present invention is directed to the use of a ligand, which ligand binds to the IL-6 receptor and signals via a gp130/LIF receptor heterodimer, in the manufacture of a medicament for the treatment of a condition characterised by unwanted lipid accumulation.

Yet still another aspect of the present invention is directed to the use of a ligand, which ligand binds to the IL-6 receptor and signals via a gp130/LIF receptor heterodimer, wherein the IL-6 receptor binding site of said ligand has a greater affinity for the IL-6 receptor than the CNTF receptor, in the manufacture of a medicament for the treatment of a condition characterised by unwanted lipid accumulation.

A further aspect of the invention provides the use of a ligand, which ligand comprises a binding site substantially similar to the IL-6R binding site of IL-6, a binding site substantially similar to the gp130 binding site of IL-6, and a binding site substantially similar to the LIF receptor binding site of CNTF, in the manufacture of a medicament for the treatment of a condition characterised by unwanted lipid accumulation.

Another further aspect provides the use of IC7 or a ligand comprising the SEQ ID NO: 7 amino acid sequence or a substantially similar ligand or a functional fragment thereof in the manufacture of a medicament for the treatment of a condition characterised by unwanted lipid accumulation.

In anther aspect, said condition is obesity, insulin resistance, glucose intolerance, dyslipidemia, non-alcoholic fatty liver disease, sleep apnea, obesity associated metabolic disorders such as osteoarthritis, type II diabetes, mellitus, hypertension, stroke or cardiovascular disease, unwanted weight gain (even where that weight gain is below the level of obesity) or body mass index and excessive appetite resulting in unwanted weight gain.

Yet another aspect of the present invention is directed to a ligand, as hereinbefore defined, which ligand is not IC7.

Still another aspect provides a pharmaceutical composition comprising a ligand as hereinbefore defined together with a pharmaceutically acceptable carrier.

In yet another aspect there is provided a ligand as hereinbefore defined for use in therapy.

DETAILED DESCRIPTION OF THE INVENTION

Figure 1:
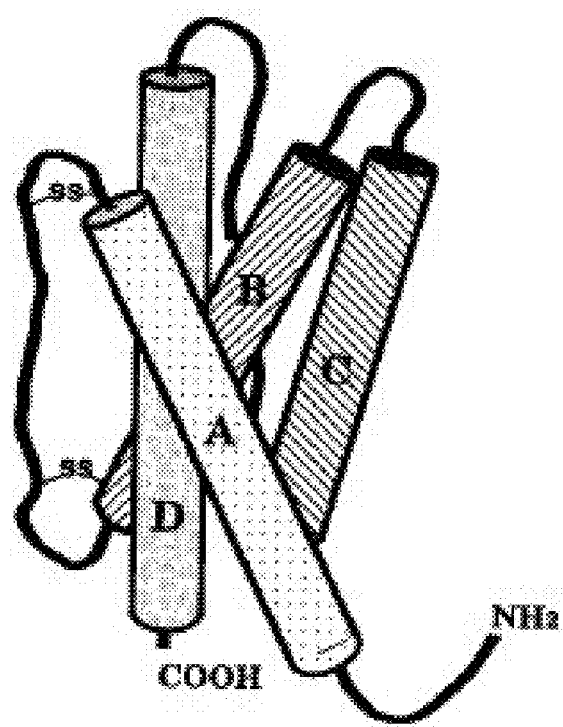
FIG. 1 is a schematic structure of IL-6.

The present invention is predicated, in part, on the determination that lipid oxidation can be induced in a mammal by administering a ligand which interacts with the IL-6 receptor and signals via a gp130/LIF receptor heterodimer. However, whereas IL-6 induced interaction with the IL-6 receptor and subsequent gp130 homodimer induced signalling can lead to inflammation, while CNTF induced interaction with the CNTF receptor, or even the IL-6 receptor, and subsequent gp130/LIF receptor heterodimer induced signalling requiring the use of high concentrations of CNTF and can lead to anti-CNTF autoantibody generation, the use of a ligand which is designed to be directed to the IL-6 receptor but signals through a gp130/LIF receptor heterodimer minimises these problems while nevertheless achieving lipid oxidation. Accordingly, this finding has now facilitated the rational design of a means for inducing lipid oxidation and, in particular, for therapeutically or prophylactically treating conditions which are characterised by unwanted lipid accumulation such as obesity, hypertension, obesity induced type II diabetes, glucose intolerance or insulin resistance.

Accordingly, one aspect of the present invention is directed to a method of inducing lipid oxidation in a mammal, said method comprising administering to said mammal a ligand which binds to the IL-6 receptor and signals via a gp130/LIF receptor heterodimer.

Without limiting the present invention to any one theory or mode of action, both IL-6 and CNTF have been found to enhance lipid oxidation and increase insulin sensitivity in mammals. To this end, IL-6 interacts with the IL-6 receptor and then signals via its further interaction with a gp130 homodimer. CNTF functions by interacting with the CNTF receptor (or with the IL-6 receptor at a significantly lower affinity) and signalling via its further interaction with a gp130/LIF receptor heterodimer. However, in addition to lipid oxidation induction, both IL-6 and CNTF are associated with less desirable functional outcomes. Specifically, the interaction of a soluble IL-6 receptor/IL-6 complex with a gp130 homodimer is linked to the induction of inflammation while CNTF, due to its lack of a secretory signal and the high concentrations at which it is required to be used in order to effect lipid oxidation in the periphery, results in CNTF autoantibody production. The inventors have determined, however, that the induction of lipid oxidation can still be effected if IL-6 receptor binding is followed by signalling via a gp130/LIF receptor heterodimer, rather than a gp130 homodimer, as is characteristic of IL-6 stimulation, but that this mechanism reduces the incidence of IL-6 related induction of inflammation. Similarly, by using a ligand which is designed to interact with the IL-6 receptor with a degree of affinity greater than that of the interaction of CNTF with the IL-6 receptor (which interaction naturally occurs due to the low level of expression of the CNTF receptor in the periphery), lower concentrations of this molecule are required to be used than if CNTF is used to induce lipid oxidation. Still further, by designing this ligand to more closely resemble IL-6 rather than CNTF, which is not secreted, the possibility of autoantibody generation is still further minimised.

Accordingly, in one embodiment the present invention is directed to a method of inducing lipid oxidation in a mammal, said method comprising administering to said mammal a ligand which binds to the IL-6 receptor and signals via a gp130/LIF receptor heterodimer wherein the IL-6 receptor binding site of said ligand has a greater affinity for the IL-6 receptor than the CNTF receptor.

In another embodiment, the IL-6 receptor binding site of said ligand is substantially similar to the IL-6 receptor binding site of IL-6.

Reference to "IL-6 receptor", 130" and "LIF receptor" should be understood as a reference to all forms of these molecules and to functional derivatives and homologues thereof. This includes, for example, any isoforms which arise from alternative splicing of the mRNA, allelic variants or mutants of these receptors.

Without limiting the present invention to any one theory or mode of action, the IL-6 receptor system consists of two membrane proteins, a ligand binding receptor (IL-6R) and a non-binding signal transducer (gp130). The human IL-6 receptor consists of 468 amino acids, including a signal peptide of 19 amino acids, an extracellular region of 339 amino acids, a membrane-spanning region of 28 amino acids, and a cytoplasmic region of 82 amino acids (Yamasaki, K et. al. (1988) Cloning and expression of the human interleukin-6 (BSF-2/IFN beta 2) receptor, Science 241:825-828) (GenBank accession number M20566, X12830). The predicted molecular weight of IL-6R is 50,000 Da, although the observed molecular weight is 80,000 Da due to N-glycosylation.

Upon binding of IL-6, IL-6R is triggered to become associated with a signal transducing receptor component, gp130 (Taga, T et. al. (1989) Interleukin-6 triggers the association of its receptor with a possible signal transducer, gp130, Cell 58:573-581). gp130 has no intrinsic IL-6 binding capability, but is involved in the formation of high-affinity IL-6 binding sites. gp130 consists of 918 amino acids, including a leader sequence of 22 amino acids, an extracellular region of 597 amino acids, a membrane-spanning region of 22 amino acids, and a cytoplasmic region of 277 amino acids (Hibi, M et. al. (1990) Molecular cloning and expression of an IL-6 signal transducer, gp130, Cell 63:1149-1157) (GenBank accession number M57230). The gp130 protein serves as a signal transducer not only for IL-6 but also for leukaemia inhibitory factor (LIF), oncostatin M (OSM), ciliary neurotrophic factor (CNTF), and IL-11 (Taga, T and Kishimoto, T 1992, Cytokine receptors and signal transduction, FASEB J 6:3387-3396; Yin, T et. al. (1993) Involvement of IL-6 signal transducer gp130 in IL-11 mediated signal transduction, J. Immunol. 151: 2555-2561). Stimulation by these cytokines induces oligomerization of the receptor components (Davis, S et. al. (1993) LIFR beta and gp130 as heterodimerizing signal transducers of the tripartite CNTF receptor, Science 260:1805-1808; Murakami, M et. al. (1993) IL-6-induced homodimerization of gp130 and associated activation of a tyrosine kinase, Science 260:1808-1810).

The CNTF receptor complex contains three proteins, a ligand binding receptor (CNTFR) that directly binds to CNTF as well as two signal transducing components—LIF receptor and gp130. cDNAs encoding CNTFα have been cloned from both human (GenBank accession number M73238) (Davis, S et. al. (1991), The receptor for ciliary neurotrophic factor, Science 253:59-63) and rat (GenBank accession number 554212) (Ip, N Y et. al. (1993a) The alpha component of the CNTF receptor is required for signalling and defines potential CNTF targets in the adult and during development, Neuron 10:89-102; Ip N Y et. al. (1993b) Injury-induced regulation of ciliary neurotrophic factor mRNA in the adult rat brain, Eur. J. Neurosci. 5:25-33). The cDNA for human CNTFRα predicts a protein precursor of 372 amino acids with putative leader sequences of approximately 20 amino acids and four conserved glycosylation sites. Glycosylation at these sites partially accounts for the difference between the observed molecular weight of CNTFR on SDS-PAGE gels (~70 kDa) and the molecular weight predicted from the amino acid sequence (~40 kDa) (Davis et. al. (1991) supra). Unlike most other growth factor receptor components, CNTFR lacks trans-membrane and intracytoplasmic domains; instead, it is anchored to the cell membrane via a GPI linkage (Davis et. al. (1991) supra). The closest known relative to CNTFR is IL-6R (30 percent amino acid identity) (Davis et. al. (1991) supra), which is a transmembrane protein.

In the absence of CNTF, the receptor components comprising the CNTF receptor complex are un-associated on the cell surface (Davis et. al. (1993) supra; Stahl, N et. al. (1993) Cross-linking identifies leukaemia inhibitory factor-binding protein as a ciliary neurotrophic factor receptor component, J. Biol. Chem. 268:7628-7631). It is this last step in receptor assembly—which involves heterodimerization between LIFR and gp130 that is responsible for transducing a signal across a membrane (Davis et. al. (1993) supra; Stahl et. al. (1993) supra).

As would be understood by the person of skill in the art, the ligand binding subunit of a receptor is referred to as the α chain while other signal transducing subunits are referred to as (3 chains and even γ chains. Accordingly, within the context of the present invention, IL-6 receptor (IL-6R), CNTF receptor (CNTFR), gp130 and LIF receptor (LIFR) are interchangeably referred to as IL-6Rα, CNTRFα, gp130β and LIFRβ.

Reference to a "ligand which binds to the IL-6 receptor and signals via a gp130/LIF receptor heterodimer" should therefore be understood as a reference to a molecule which, although initially binding the IL-6 receptor thereafter engages a CNTF-like signalling mechanism, being the association of the IL-6 receptor/ligand complex with gp130 and its heterodimerization with LIF receptor in order to effect intracellular signalling.

Reference to a "ligand" should be understood as a reference to a molecule which binds to and activates a receptor complex. In terms of designing a ligand molecule capable of binding to the IL-6 receptor and signalling via a gp130/LIF receptor heterodimer, and as detailed above, the amino acid sequence and 3-dimensional structure of these receptors are well known, as are the actual ligand binding regions. Similarly, the sequences and 3-dimensional structures of IL-6 and CNTF are also well known.

Specifically, human IL-6 consists of 212 amino acids including a 28 amino acid signal peptide (SEQ ID NO: 1) (Hirano, T et. al. (1986) Complementary DNA for a novel human interleukin (BSF-2) that induces B lymphocytes to produce immunoglobulin, *Nature* 324:73-6) (GenBank accession number X04602). Human IL-6 is a secreted glycoprotein containing 184 amino acids in the mature protein (SEQ ID NO: 2). The molecular weight of the core protein is about 20,000 Da. The two disulphide bridges have been located between Cys44-Cys50 and Cys73-Cys83 in human IL-6 (Simpson, R J et. al. (1988) Characterization of a recombinant murine interleukin-6: assignment of disulphide bonds, *Biochem. Biophys. Res. Commun.* 157:364-372). The molecular weight of natural IL-6 is 21-26,000 Da depending on the cellular source. Its heterogeneity results from post-translational modifications such as N- and O-linked glycosylation and phosphorylation (position 45 and 144 in human IL-6 are N-glycosylated). IL-6 has a tertiary fold which is similar to the four-α-helix bundle structure found in growth hormone, despite little similarity in amino acid sequence to growth hormone (Bazan, J F (1990a) Haemopoietic receptors and helical cytokines, *Immunol. Today* 11:350-354; Bazan, J F (1990b) Structural design and molecular evolution of a cytokine receptor superfamily, *Proc. Natl. Acad. Sci.* (USA) 87:6934-6938). The four α-helices (labelled A to D in FIG. 1) and loops (two long A-B and C-D loops, and a short B-C loop) predicted in the IL-6 protein are adopted in other cytokines, such as CNTF.

Genes and cDNAs encoding CNTF have been cloned from human (GenBank accession numbers 60477-8, 60542, 55889-90) (McDonald, J R et. al. (1991), Expression and characterization of recombinant human ciliary neurotrophic factor from *Escherichia coli.*, *Biochim. Biophys. Acta* 1090: 70-80; Masiakowski, P et. al. (1991) Recombinant human and rat ciliary neurotrophic factors, J. Neurochem. 57:1003-1012). The human CNTF protein is 200 amino acids in length (SEQ ID NO:3). CNTF is not secreted but rather found in the cytoplasm of cells, such as astrocytes (Rudge, J S et. al. (1992) Expression of ciliary neurotrophic factor and the neurotrophins—nerve growth factor brain-derived neurotrophic factor and neurotrophin-3—in cultured rat hippocampal astrocytes, *Eur. J. Neurosci.* 4:459-471; Rende, M et. al. (1992) Immunolocalization of ciliary neuroneotrophic factor in adult rat sciatic nerve, *Glia* 5:25-32; Friedman, B et. al. (1992) Regulation of ciliary neurotrophic factor expression in myelin-related Schwann cells in vivo, *Neuron* 9:295-305), which express CNTF. CNTF is a member of a cytokine subfamily that includes LIF, IL-6, and OSM (Bazan, J F (1991) Neuropoietic cytokines in the hematopoietic fold, *Neuron* 7:197-208). Though these four factors exhibit minimal primary sequence homology, they all share secondary structural features which link them and allow them to conform generally to the four-α helix bundle structure first described for growth hormone and depicted in FIG. 1 (Bazan (1991) supra).

In terms of the binding of IL-6 and CNTF to their respective a receptors, for IL-6 and CNTF the contact site with the receptor α-unit can be mapped to a site that includes residues of the C-terminal AB loop and the C-terminal D-helix (site I) (McDonald et. al. (1995), *EMBO J.* 14:2689-2699; Panayotatos, N et. al. (1995), *J. Biol. Chem.* 270: 14007-14014; Grotzinger, J et. al. (1997) *Proteins Struct. Funct. Genet.* 27:96-109). Residues of the A- and C-helices of CNTF and IL-6 constitute a gp130-binding site (site II). In IL-6, a second gp130-binding site consists of amino acids residues of the N-terminal AB loop, the C-terminal CD loop, and the N-terminal D-helix. This site is termed site III. Crystallographic and mutagenesis studies of CNTF and LIF indicate that residues of the C-terminal B-helix, possibly the BC loop, CD loop, and the N-terminal D-helix constitute site III in these cytokines (McDonald et. al. (1995), supra; Panayotatos, N et. al. (1995), supra) (see FIG. 2).

Figure 2:
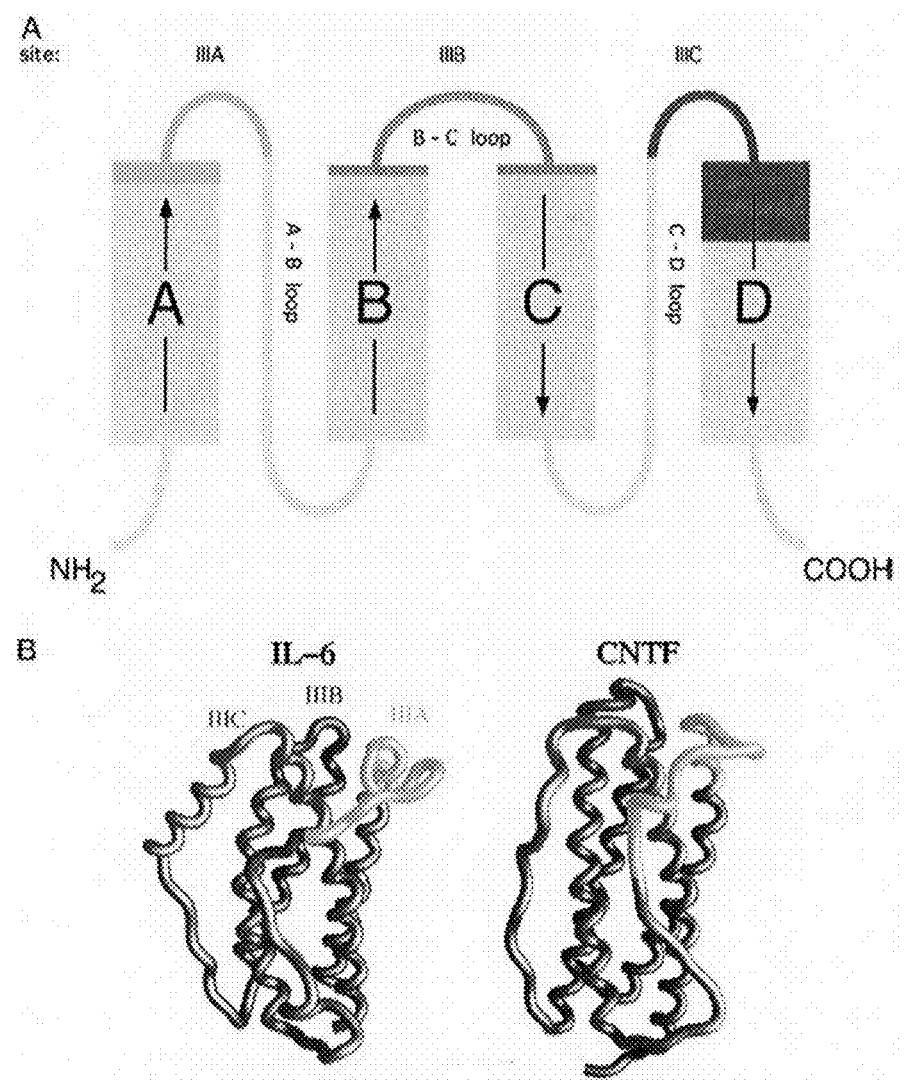
FIG. 2 depicts the site III gp130 and LIFR binding epitope of IL-6 and CNTF, respectively. (a) schematic drawing of the common four-helix bundle cytokine fold. (b) ribbon models of the IL-6 NMR and CNTF x-ray structures. The different parts of site III are identified as site IIIA, site IIIB, and site IIIC.

Considering the conserved four-helical bundle structure of IL-6 and CNTF these cytokines have evolved as discontinuous modules which are exchangeable (FIG. 2).

Accordingly, in one embodiment the present invention is directed to a method of inducing lipid oxidation in a mammal, said method comprising administering to said mammal a ligand comprising an IL-6 receptor binding site, a gp130 binding site and a LIF receptor binding site.

In another embodiment, said IL-6 receptor binding site exhibits greater affinity for IL-6Rα than CNTFRα.

In still another embodiment, the IL-6 receptor binding site of said ligand is substantially similar to the IL-6 receptor binding site of IL-6.

This aspect of the present invention therefore provides a method of inducing lipid oxidation in a mammal, said method comprising administering to said mammal a ligand comprising a binding site substantially similar to the IL-6R binding site of IL-6, a gp130 binding site and a LIF receptor binding site.

Still more particularly there is provided a method of inducing lipid oxidation in a mammal, said method comprising administering to said mammal a ligand comprising a binding site substantially similar to the IL-6R binding site of IL-6, a binding site substantially similar to the gp130 binding site of IL-6 and a binding site substantially similar to the LIF receptor binding site of CNTF.

The phrase "substantially similar" in the context of two polypeptides, can refer to two or more sequences that have, e.g., at least about at least 90%, 91%, 92%, 93%, 94%, 95%, 96%, 97%, 98%, 99% or more amino acid residue (sequence) identity, when compared and aligned for maximum correspondence, as measured using one any known sequence comparison algorithm, as discussed below, or by visual inspection.

Because two polypeptides may each comprise (1) a sequence (i.e. only a portion of the complete polynucleotide sequence) that is similar between the two polypeptides, and (2) a sequence that is divergent between the two polypeptides, sequence comparisons between two (or more) polypeptides are typically performed by comparing sequences of the two polypeptides over a "comparison window" to identify and compare local regions of sequence similarity. A "comparison window", as used herein, includes reference to a segment of any one of the numbers of contiguous residues. For example, in alternative aspects of the invention, contiguous residues ranging anywhere from 5 to the full length of an exemplary polypeptide sequence of the invention are compared to a reference sequence of the same number of contiguous positions after the two sequences are optimally aligned. If the reference sequence has the requisite sequence identity to an exemplary polypeptide of the invention, that sequence is within the scope of the invention.

The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as for example disclosed by Altschul et al. (1997) Nucl. Acids Res. 25:3389. A detailed discussion of sequence analysis can be found in Unit 19.3 of Ausubel et al. ("Current Protocols in Molecular Biology" John Wiley & Sons Inc, Chapter 15, 1994-1998). A range of other algorithms may be used to compare the nucleotide and amino acid sequences such as but not limited to PILEUP, CLUSTALW, SEQUENCHER or VectorNTI.

The terms "sequence similarity" and "sequence identity" as used herein refers to the extent that sequences are identical or functionally or structurally similar on a residue-by-residue basis over a window of comparison. Thus, a "percentage of sequence identity", for example, is calculated by comparing two optimally aligned sequences over the window of comparison, determining the number of positions at which the identical amino acid occurs in both sequences to yield the number of matched positions, dividing the number of matched positions by the total number of positions in the window of comparison (i.e., the window size), and multiplying the result by 100 to yield the percentage of sequence identity.

Protein sequence identities (homologies) may be evaluated using any of the variety of sequence comparison algorithms and programs known in the art. The extent of sequence identity (homology) may be determined using any computer program and associated parameters, including those described herein, such as BLAST 2.2.2. or FASTA version 3.0t78, with the default parameters.

The terms "homology" and "identity" in the context of two or more polypeptide sequences, refer to two or more sequences that are the same or have a specified percentage of amino acid residues or nucleotides that are the same when compared and aligned for maximum correspondence over a comparison window or designated region as measured using any number of sequence comparison algorithms or by manual alignment and visual inspection. For sequence comparison, one sequence can act as a reference sequence to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

In yet another embodiment, said ligand comprises sites I and II of IL-6, or substantially similar sites as hereinbefore defined and site III of CNTF or substantially similar site.

Accordingly to these embodiments, the subject ligand is an IL-6/CNTF chimeric protein. More specifically, an exemplary chimera is one in which the site III loop of CNTF is inserted in IL-6 in place of the site III loop of IL-6. In such chimeras, amino acid residues located in the C-terminal A-helix, the N-terminal AB loop (Glu36-Met56; SEQ ID NO:4) of CNTF may be substituted in place of the IL-6 residues between Arg40-Asn60 (i.e., Arg40 and Asn60 are retained), the C-terminal CD loop with the adjoining N-terminal D helix (Gly147-Leu162; SEQ ID NO:6) of CNTF may be substituted in place of IL-6 residues between Leu151-Arg168 and the BC loop with adjacent parts of B- and C-helix (Leu91-Ile109; SEQ ID NO:5) of CNTF may be substituted in place of the IL-6 residues between Leu101-Arg113.

Preferably, said ligand is IC7, as described in Kallen et. al. (1999) supra or SEQ ID NO: 7 or a substantially similar ligand.

The method of the present invention should also be understood to extend to the use of functional fragments of IC7 or SEQ ID NO:7. Reference to "functional" should be understood as a reference to a fragment which is capable of binding to the IL-6 receptor and signalling via a gp130/LIF receptor heterodimer.

According to this embodiment there is provided a method of inducing lipid oxidation in a mammal, said method comprising administering to said mammal IC7, a ligand comprising the SEQ ID NO:7 amino acid sequence or a substantially similar ligand or functional fragment thereof.

The invention also extends to functional variants of the subject ligand which have one or more amino acid substitutions, additions and deletions. There may be 1 to 5, 5 to 10, 10 to 15, 15 to 20, 20 to 30 or more residues substituted, added or deleted, whilst maintaining functionality.

Substitutions encompass amino acid alterations in which an amino acid is replaced with a different naturally-occurring or a non-conventional amino acid residue. Such substitutions may be classified as "conservative", in which case an amino acid residue present in a peptide is replaced with another naturally-occurring amino acid of similar character, for example Gly to Ala, Asp to Glu, Asn to Gln or Trp to Tyr. Possible alternative amino acids include Serine or Threonine, Aspartic acid or Glutamic acid or γ-Carboxyglutamate, Proline or Hydroxyproline, Arginine or Lysine, Asparagine or Histidine, Histidine or Asparagine, Tyrosine or Phenylalanine or Tryptophan, Aspartate or Glutamate, Isoleucine or Leucine or Valine.

Such conservative substitutions are shown in Table 1 under the heading of preferred substitutions. If such substitutions do not result in a change in functional activity, then more substantial changes, denoted exemplary substitutions in Table 1, or as further described below in reference to amino acid classes, may be introduced, and the resulting variant analyzed for functional activity.

TABLE 1

| | Amino acid substitutions | |
|---|---|---|
| Original Residue | Exemplary Substitutions | Preferred Substitutions |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |

TABLE 1-continued

Amino acid substitutions

| Original Residue | Exemplary Substitutions | Preferred Substitutions |
|---|---|---|
| Glu (E) | asp | asp |
| Gly (G) | pro | pro |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Substitutions encompassed by the present invention may also be "non-conservative", in which an amino acid residue which is present in a polypeptide is substituted with an amino acid having different properties, such as a naturally-occurring amino acid from a different group (e.g. substituting a charged or hydrophilic or hydrophobic amino acid with Alanine), or alternatively, in which a naturally-occurring amino acid is substituted with a non-conventional amino acid. Additions encompass the addition of one or more naturally occurring or non-conventional amino acid residues. Deletions encompass the deletion of one or more amino acid residues.

Methods for combinatorial synthesis of analogues of the ligand and for screening of the analogues to determine that they retain activity are well known in the art (see for example Gallop et al. (1994) *J. Med. Chem.* 37:1233-1251; Hogan (1997) *Nature Biotechnology* 15:328-330).

Non-conventional amino acids or chemical amino acid analogues can be used in place of naturally occurring amino acid molecules. Thus for example Leucine may be replaced by Norleucine, Valine may be replaced by Norvaline, Cysteine may be replaced by Homocysteine, Serine may be replaced by Homoserine, Lysine may be replaced by 5-Hydroxylysine, Proline by 4-Hydroxyproline, Arginine may be replaced by Homoarginine, Ornithine or Citrulline, Alanine may be replaced by α-Methylalanine or β-Alanine, a D-amino acid may be used instead of the corresponding L-amino acid, any amino acid may be N-methylated, or the N-terminus may be acetylated. A non-conventional amino acid further includes one selected from the group consisting of D-amino acids, homo-amino acids, N-alkyl amino acids, dehydroamino acids, aromatic amino acids (other than phenylalanine, tyrosine and tryptophan), ortho-, meta- or para-aminobenzoic acid, ornithine, citrulline, norleucine, γ-glutamic acid, aminobutyric acid (Abu), and α-αdisubstituted amino acids.

Non-conventional amino acids also include compounds which have an amine and carboxyl functional group separated in a 1,3 or larger substitution pattern, such as β-alanine, β-amino butyric acid, Freidinger lactam, the bicyclic dipeptide (BTD), amino-methyl benzoic acid and others well known in the art. Statine-like isosteres, hydroxyethylene isosteres, reduced amide bond isosteres, thioamide isosteres, urea isosteres, carbamate isosteres, thioether isosteres, vinyl isosteres and other amide bond isosteres known to the art may also be used.

The use of analogues or non-conventional amino acids may improve the stability and biological half-life of the subject ligand. The person skilled in the art will be aware of similar types of substitution which may be made.

A non limiting list of non-conventional amino acids which may be used as suitable replacements for the naturally occurring amino acids and their standard abbreviations is set out in Table 2.

TABLE 2

Non-conventional amino acids

| Non-conventional amino acid | Abbrev. | Non-conventional amino acid | Abbrev. |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |

TABLE 2-continued

Non-conventional amino acids

| Non-conventional amino acid | Abbrev. | Non-conventional amino acid | Abbrev. |
|---|---|---|---|
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | arg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl)carbamylmethyl)glycine | Nnbhm | N-(N-(3,3-diphenylpropyl)carbamylmethyl)glycine | Nnbhe |
| 1-carboxy-1-(2,2-diphenyl-ethylamino)cyclopropane | Nmbc | L-O-methyl serine | Omser |
| | | L-O-methyl homoserine | Omhser |

It is to be understood that the invention also encompasses analogues of the subject ligand which include but are not limited to the following:
  (i) ligands in which one or more amino acids is replaced by its corresponding D-amino acid. The skilled person will be aware that such sequences, including retro-inverso amino acid sequences where substantially all of the amino acids are D-amino acids and the order is reversed can be synthesised by standard methods; see for example Chorev and Goodman (1993) *Acc. Chem. Res.* 26:266-273;
  (ii) peptidomimetic compounds, in which a peptide bond of the ligand is replaced by a structure more resistant to metabolic degradation. See for example Olson et al. (1993) *J. Med. Chem.* 36:3039-3049; and
  (iii) ligands in which individual amino acids are replaced by analogous structures, for example, gem-diamino-alkyl groups or alkylmalonyl groups, with or without modified termini or alkyl, acyl or amine substitutions to modify their charge.

It should be understood that the subject ligand may be glycosylated or unglycosylated and/or may contain a range of other proteinaceous or non-proteinaceous molecules fused, linked, bound or otherwise associated to the ligand such as amino acids, lipids, carbohydrates or other peptides, polypeptides or proteins. Reference hereinafter to a "ligand" includes a ligand comprising a sequence of amino acids as well as a ligand associated with other molecules such as amino acids, lipids, carbohydrates or other peptides, polypeptides or proteins. For example, the ligand may be linked to a proteinaceous or non-proteinaceous molecule which can facilitate steric hindrance of the subject ligand in terms of it crossing the blood-brain barrier is suitable for use. In one embodiment, the invention provides a ligand complexed to the Fc portion of IgG.

Ligands of the invention can be isolated from natural sources, be synthetic, or be recombinantly generated polypeptides. Peptides and proteins can be recombinantly expressed in vitro or in vivo. The ligands of the invention can be made and isolated using any method known in the art. The ligands can also be synthesized, whole or in part, using chemical methods well known in the art. See e.g., Caruthers (1980) *Nucleic Acids Res. Symp. Ser.* 215-223; Horn (1980) *Nucleic Acids Res. Symp. Ser.* 225-232; Banga, A. K. (1995) *Therapeutic Peptides and Proteins*, Formulation, Processing and Delivery Systems, Technomic Publishing Co., Lancaster, Pa. For example, peptide synthesis can be performed using various solid-phase techniques (see e.g., Roberge (1995) *Science* 269:202; Merrifield (1997) *Methods Enzymol.* 289:3-13) and automated synthesis may be achieved, e.g., using the ABI 431A Peptide Synthesizer (Perkin Elmer) in accordance with the instructions provided by the manufacturer. For example, the CNTF/IL-6 chimeric ligand of the present invention may be generated by directly linking or joining via a linker the subject receptor binding regions.

The ligand of the invention can also be synthesised and expressed as a fusion protein with one or more additional domains linked thereto for, e.g., to more readily isolate a recombinantly synthesized ligand or to prevent transport of the ligand across the blood-brain barrier. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.) may also be used. The inclusion of a cleavable linker sequences such as Factor Xa or enterokinase (Invitrogen, San Diego Calif.) between a purification domain and the motif-comprising protein to facilitate purification. For example, an expression vector can include an epitope-encoding nucleic acid sequence linked to six histidine residues followed by a thioredoxin and an enterokinase cleavage site (see e.g., Williams (1995) *Biochemistry* 34:1787-1797; Dobeli (1998) *Protein Expr. Purif.* 12:404-414). The histidine residues facilitate detection and purification while the enterokinase cleavage site provides a means for purifying a region from the remainder of the fusion protein. Technology pertaining to vectors encoding fusion proteins and application of fusion proteins are well described in the scientific and patent literature, see e.g., Kroll (1993) *DNA Cell. Biol.* 12:441-453.

The method of the present invention is directed to inducing lipid oxidation in a mammal and thereby providing a means of preventing, retarding or reversing lipid accumulation. Since lipid accumulation leads to fat deposition and subsequently to a broad range of direct or indirect complications including, but not limited to, obesity, insulin resistance, glucose intolerance, dyslipidemia, hypertension, osteoarthritis, type II diabetes, stroke, cardiovascular diseases, the method of the present invention provides a wide range of potential applications.

Reference to "lipid" should be understood in its broadest sense to encompass any member of the group of oils, fats and fat-like substances which are found in tissue including, for example, (1) fatty acids; (2) neutral fats (i.e. triacylglycerols), other fatty-acid esters; (3) long-chain (or fatty) alcohols and waxes; (4) sphingoids and other long-chain bases; (5) glycolipids, phospholipids, and sphingolipids; and (6) carotenes, polyprenols, sterols (and related compounds), terpenes, and other isoprenoids.

The term "mammal" as used herein includes humans, primates, livestock animals (eg. horses, cattle, sheep, pigs, donkeys), laboratory test animals (eg. mice, rats, guinea pigs), companion animals (eg. dogs, cats) and captive wild animal (eg. kangaroos, deer, foxes). Preferably, the mammal is a human or a laboratory test animal. Even more preferably, the mammal is a human.

In a related aspect, it has also been determined that although the ligand hereinbefore defined increases lipid oxidation, this ligand is also useful for increasing the insulin sensitivity of a mammal independently of the induction of changes to lipid oxidation. Without limiting the present invention to any one theory or mode of action it is thought that insulin sensitivity is increased by virtue of the activation of AMP activated protein kinase.

Accordingly, a related aspect of the present invention is directed to a method of increasing insulin sensitivity in a mammal, said method comprising administering to said mammal a ligand as hereinbefore defined.

Reference to "insulin sensitivity" should be understood as a reference to the functional responsiveness of a mammal or mammalian tissue to stimulation by insulin. Without limiting the present invention in any way, insulin stimulates glucose uptake by muscle and adipose tissue and promotes glycogenesis, lipogenesis, synthesis of protein and nucleic acid. Accordingly, reference to "increased" insulin sensitivity should be understood as an increased level of any one or more of the functional outcomes of insulin stimulation relative to the levels evident in the mammal prior to application of the method of the invention. For example, one may observe increased glucose uptake.

As detailed hereinbefore, a further aspect of the present invention relates to the use of the invention in relation to the treatment or prophylaxis of disease conditions or other unwanted conditions.

Accordingly, another aspect of the present invention is directed to a method of therapeutically or prophylactically treating a condition in a mammal, which condition is characterised by unwanted lipid accumulation, said method comprising administering to said mammal a ligand which binds to the IL-6 receptor and signals via a gp130/LIF receptor heterodimer.

More particularly, the present invention is directed to a method of therapeutically or prophylactically treating a condition in a mammal, which condition is characterised by unwanted lipid accumulation, said method comprising administering to said mammal a ligand which binds to the IL-6 receptor and signals via a gp130/LIF receptor heterodimer, wherein the IL-6 receptor binding site of said ligand has a greater affinity for the IL-6 receptor than the CNTF receptor.

In one embodiment, the IL-6 receptor binding site of said ligand is substantially similar to the IL-6 receptor binding site of IL-6.

In another embodiment, said ligand comprises an IL-6 receptor binding site, a gp130 binding site and a LIF receptor binding site.

This aspect of the invention therefore provides a method of therapeutically or prophylactically treating a condition in a mammal, which condition is characterised by unwanted lipid accumulation, said method comprising administering to said mammal a ligand comprising a binding site substantially similar to the IL-6R binding site of IL-6, a binding site substantially similar to the gp130 binding site of IL-6, and a binding site substantially similar to the LIF receptor binding site of CNTF.

In yet another embodiment, said ligand comprises sites I and II of IL-6 or substantially similar sites and site III of CNTF or substantially similar site.

Preferably, said ligand is IC7 or a ligand comprising the SEQ ID NO: 7 amino acid sequence or a substantially similar ligand or a functional fragment thereof.

This embodiment therefore provides a method of therapeutically or prophylactically treating a condition in a mammal, which condition is characterised by unwanted lipid accumulation, said method comprising administering to said mammal IC7, a ligand comprising the SEQ ID NO:7 amino acid sequence or a substantially similar ligand or functional fragment thereof.

Reference to a condition "characterised by unwanted lipid accumulation" should be understood as a reference to any condition in respect of which lipid accumulation is either a cause or symptom. To this end, in the context of some conditions, increasing lipid oxidation may either treat the cause of the disease condition or at least relieve a symptom associated with the condition. Examples of conditions characterised by unwanted lipid accumulation include, but are not limited to obesity, insulin resistance, glucose intolerance, dyslipidemia, non-alcoholic fatty liver disease, sleep apnea, obesity associated metabolic disorders such as osteoarthritis, type II diabetes mellitus, hypertension, stroke or cardiovascular disease, unwanted weight gain (even where that weight gain is below the level of obesity) or body mass index and excessive appetite resulting in unwanted weight gain.

The terms "obesity" and "obese" generally refer to individuals whose body weight is at least 20% above the average body weight for the individual's age, gender and height. An individual is also defined as "obese" if the individual is a male whose body mass index is greater than 27.8 kg/m.sup.2 or a female whose body mass index is greater than 27.3 kg/m.sup.2. Those of skill in the art will recognize that individuals can be significantly above the average weight for their age, gender, and height and still technically not be "obese." Such individuals are referred to as "overweight" herein, in accordance with normal usage. This invention will be beneficial for such overweight individuals, and may also be beneficial to individuals who are prone to obesity or to being overweight and who wish to avoid a recurrence of earlier episodes of obesity or being overweight.

The term "obesity-associated metabolic disorder" means a disorder which results from, is a consequence of, is exacerbated by or is secondary to obesity. Non-limiting examples of such a disorder are osteoarthritis, Type II diabetes mellitus, increased blood pressure, stroke, and heart disease.

To this end, it should be understood that although the method of the present invention has particular application in the context of obese individuals, this is not a limitation to the application of the invention. Rather, the method of the invention can be applied in any situation in which lipid accumulation is unwanted, such as in the context of an athlete, where the alteration of overall body mass composition may be sought, or improving appearance or body image.

In a related aspect there is provided a method of therapeutically or prophylactically treating a condition in a mammal, which condition is characterised by inadequate insulin sensitivity, said method comprising administering to said mammal a ligand as hereinbefore defined.

Reference to a "condition characterised by inadequate insulin sensitivity" should be understood as a reference to any condition in which the level of insulin responsiveness of the mammal is inadequate or otherwise insufficient for its physiological needs, irrespective of whether said inadequate insulin sensitivity is a cause or a symptom of said condition. Examples of such conditions include, but are not limited to diabetes mellitus, insulin resistance, glucose intolerance, obesity, dyslipidemia, liver disease, metabolic disorders, hypertension, cardiovascular disease or stroke.

These therapeutic and prophylactic aspects of the present invention are preferably achieved by administering an effective amount of the ligand, as hereinbefore defined, for a time and under conditions sufficient to appropriately modulate lipid oxidation.

An "effective amount" means an amount necessary to at least partly to attain the desired response, or to delay the onset or inhibit progression or halt altogether, the onset or progression of the particular condition being treated. The amount varies depending upon the health and physical condition of the individual to be treated, the taxonomic group of the individual to be treated, the degree of protection desired, the formulation of the composition, the assessment of the medical situation, and other relevant factors. It is expected that the amount will fall in a relatively broad range that can be determined through routine trials.

Reference herein to "treatment" and "prophylaxis" is to be considered in its broadest context. The term "treatment" does not necessarily imply that a subject is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity or onset of a particular condition. "Treatment" may also reduce or retard the severity or progression of an existing condition.

The present invention further contemplates a combination of therapies, such as the administration of the ligand together with other proteinaceous or non-proteinaceous molecules which may facilitate the desired therapeutic or prophylactic outcome. For example, one may combine the method of the present invention with appetite suppression therapy, cholesterol medication, insulin administration or the like.

Administration of the ligand of the present invention in the form of a pharmaceutical composition, may be performed by any convenient means. The ligand is contemplated to exhibit therapeutic activity when administered in an amount which depends on the particular case. The variation depends, for example, on the human or animal. A broad range of doses may be applicable. Considering a patient, for example, from about 0.1 µg to about 1 mg of ligand may be administered per kilogram of body weight per day. Dosage regimes may be adjusted to provide the optimum therapeutic response. For example, several divided doses may be administered daily, weekly, monthly or other suitable time intervals or the dose may be proportionally reduced as indicated by the exigencies of the situation.

The ligand may be administered in a convenient manner such as by the oral, intravenous (where water soluble), respiratory, transdermal, intraperitoneal, intramuscular, subcutaneous, intradermal or suppository routes or implanting (e.g. using slow release molecules). The ligand may be administered in the form of pharmaceutically acceptable nontoxic salts, such as acid addition salts or metal complexes, e.g. with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the ligand is to be administered in tablet form, the tablet may contain a binder such as tragacanth, corn starch or gelatin; a disintegrating agent, such as alginic acid; and a lubricant, such as magnesium stearate.

Routes of administration include, but are not limited to, respiratorally, transdermally, intratracheally, nasopharyngeally, intravenously, intraperitoneally, subcutaneously, intracranially, intradermally, intramuscularly, intraoccularly, intrathecally, intracereberally, intranasally, infusion, orally, rectally, via IV drip, patch and implant.

In accordance with these methods, the ligand may be coadministered with one or more other compounds or molecules. By "coadministered" is meant simultaneous administration in the same formulation or in two different formulations via the same or different routes or sequential administration by the same or different routes. For example, the subject ligand may be administered together with an agonistic agent in order to enhance its effects. By "sequential" administration is meant a time difference of from seconds, minutes, hours or days between the administration of the two types of molecules. These molecules may be administered in any order.

Yet another aspect of the present invention is directed to the use of a ligand, which ligand binds to the IL-6 receptor and signals via a gp130/LIF receptor heterodimer, in the manufacture of a medicament for the treatment of a condition characterised by unwanted lipid accumulation.

More particularly, the present invention is directed to the use of a ligand, which ligand binds to the IL-6 receptor and signals via a gp130/LIF receptor heterodimer, wherein the IL-6 receptor binding site of said ligand has a greater affinity for the IL-6 receptor than the CNTF receptor, in the manufacture of a medicament for the treatment of a condition characterised by unwanted lipid accumulation.

In one embodiment, the IL-6 receptor binding site of said ligand is substantially similar to the IL-6 receptor binding site of IL-6.

In another embodiment, said ligand comprises an IL-6 receptor binding site, a gp130 binding site and a LIF receptor binding site.

This aspect of the invention therefore provides the use of a ligand, which ligand comprises a binding site substantially similar to the IL-6R binding site of IL-6, a binding site substantially similar to the gp130 binding site of IL-6, and a binding site substantially similar to the LIF receptor binding site of CNTF, in the manufacture of a medicament for the treatment of a condition characterised by unwanted lipid accumulation.

In yet another embodiment, said ligand comprises sites I and II of IL-6 or substantially similar sites and site III of CNTF or substantially similar site.

Preferably, said ligand is IC7 or a ligand comprising the SEQ ID NO: 7 amino acid sequence or a substantially similar ligand or a functional fragment thereof.

This embodiment therefore provides the use of IC7 or a ligand comprising the SEQ ID NO: 7 amino acid sequence or a substantially similar ligand or a functional fragment thereof in the manufacture of a medicament for the treatment of a condition characterised by unwanted lipid accumulation.

Preferably, said condition is obesity, insulin resistance, glucose intolerance, dyslipidemia, non-alcoholic fatty liver disease, sleep apnea, obesity associated metabolic disorders such as osteoarthritis, type II diabetes, mellitus, hypertension, stroke or cardiovascular disease, unwanted weight gain (even where that weight gain is below the level of obesity) or body mass index and excessive appetite resulting in unwanted weight gain.

Yet another aspect of the present invention is directed to the use of the ligand as hereinbefore defined in the manufacture of a medicament for the treatment of a condition characterised by inadequate insulin sensitivity.

Preferably, said condition is diabetes mellitus, insulin resistance, glucose intolerance, obesity, dyslipidemia, liver disease, metabolic disorders, hypertension, cardiovascular disease or stroke.

The ligand of the invention can be combined with a pharmaceutically acceptable carrier (excipient) to form a pharmacological composition. Pharmaceutically acceptable carriers can contain a physiologically acceptable compound that acts to, e.g., stabilize, or increase or decrease the absorption or clearance rates of the pharmaceutical compositions of the invention. Physiologically acceptable compounds can include, e.g., carbohydrates, such as glucose, sucrose, or dextrans, antioxidants, such as ascorbic acid or glutathione, chelating agents, low molecular weight proteins, compositions that reduce the clearance or hydrolysis of the peptides or polypeptides, or excipients or other stabilizers and/or buffers. Detergents can also used to stabilize or to increase or decrease the absorption of the pharmaceutical composition, including liposomal carriers. Pharmaceutically acceptable carriers and formulations for peptides and polypeptides are known to the skilled artisan and are described in detail in the scientific and patent literature, see e.g., the latest edition of Remington's Pharmaceutical Science, Mack Publishing Company, Easton, Pa. ("Remington's").

Other physiologically acceptable compounds include wetting agents, emulsifying agents, dispersing agents or preservatives which are particularly useful for preventing the growth or action of microorganisms. Various preservatives are well known and include, e.g., phenol and ascorbic acid. One skilled in the art would appreciate that the choice of a pharmaceutically acceptable carrier including a physiologically acceptable compound depends, for example, on the route of administration of the peptide or polypeptide of the invention and on its particular physio-chemical characteristics.

In one aspect, a solution of ligand is dissolved in a pharmaceutically acceptable carrier, e.g., an aqueous carrier if the composition is water-soluble. Examples of aqueous solutions that can be used in formulations for enteral, parenteral or transmucosal drug delivery include, e.g., water, saline, phosphate buffered saline, Hank's solution, Ringer's solution, dextrose/saline, glucose solutions and the like. The formulations can contain pharmaceutically acceptable auxiliary substances as required to approximate physiological conditions, such as buffering agents, tonicity adjusting agents, wetting agents, detergents and the like. Additives can also include additional active ingredients such as bactericidal agents, or stabilizers. For example, the solution can contain sodium acetate, sodium lactate, sodium chloride, potassium chloride, calcium chloride, sorbitan monolaurate or triethanolamine oleate. These compositions can be sterilized by conventional, well-known sterilization techniques, or can be sterile filtered. The resulting aqueous solutions can be packaged for use as is, or lyophilized, the lyophilized preparation being combined with a sterile aqueous solution prior to administration. The concentration of protein in these formulations can vary widely, and will be selected primarily based on fluid volumes, viscosities, body weight and the like in accordance with the particular mode of administration selected and the patient's needs.

Solid formulations can be used for enteral (oral) administration. They can be formulated as, e.g., pills, tablets, powders or capsules. For solid compositions, conventional nontoxic solid carriers can be used which include, e.g., pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10% to 95% of active ingredient (e.g., peptide). A non-solid formulation can also be used for enteral administration. The carrier can be selected from various oils including those of petroleum, animal, vegetable or synthetic origin, e.g., peanut oil, soybean oil, mineral oil, sesame oil, and the like. Suitable pharmaceutical excipients include e.g., starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol.

The ligands of the invention, when administered orally, can be protected from digestion. This can be accomplished either by complexing the peptide or polypeptide with a composition to render it resistant to acidic and enzymatic hydrolysis or by packaging the peptide or polypeptide in an appropriately resistant carrier such as a liposome. Means of protecting compounds from digestion are well known in the art, see, e.g., Fix (1996) *Pharm Res.* 13:1760-1764; Samanen (1996) *J. Pharm. Pharmacol.* 48:119-135; U.S. Pat. No. 5,391,377, describing lipid compositions for oral delivery of therapeutic agents (liposomal delivery is discussed in further detail, infra).

Systemic administration can also be by transmucosal or transdermal means. For transmucosal or transdermal administration, penetrants appropriate to the barrier to be permeated can be used in the formulation. Such penetrants are generally known in the art, and include, e.g., for transmucosal administration, bile salts and fusidic acid derivatives. In addition, detergents can be used to facilitate permeation. Transmucosal administration can be through nasal sprays or using suppositories. See, e.g., Sayani (1996) Systemic delivery of peptides and proteins across absorptive mucosae, *Crit. Rev. Ther. Drug Carrier Syst.* 13:85-184. For topical, transdermal administration, the agents are formulated into ointments, creams, salves, powders and gels. Transdermal delivery systems can also include, e.g., patches.

The ligands of the invention can also be administered in sustained delivery or sustained release mechanisms, which can deliver the formulation internally. For example, biodegradeable microspheres or capsules or other biodegradable polymer configurations capable of sustained delivery of a peptide can be included in the formulations of the invention (see, e.g., Putney (1998) *Nat. Biotechnol.* 16:153-157).

For inhalation, the ligands of the invention can be delivered using any system known in the art, including dry powder aerosols, liquids delivery systems, air jet nebulizers, propellant systems, and the like. See, e.g., Patton (1998) *Biotechniques* 16:141-143; product and inhalation delivery systems for polypeptide macromolecules by, e.g., Dura Pharmaceuticals (San Diego, Calif.), Aradigm (Hayward, Calif.), Aerogen (Santa Clara, Calif.), Inhale Therapeutic Systems (San Carlos, Calif.), and the like. For example, the pharmaceutical formulation can be administered in the form of an aerosol or mist. For aerosol administration, the formulation can be supplied in finely divided form along with a surfactant and propellant. In another aspect, the device for delivering the formulation to respiratory tissue is an inhaler in which the formulation vaporizes. Other liquid delivery systems include, e.g., air jet nebulizers.

Further, in another embodiment, the ligand may be administered by intravenous, intraarterial, or intramuscular injection of a liquid preparation. Suitable liquid formulations include solutions, suspensions, dispersions, emulsions, oils and the like. In one embodiment, the pharmaceutical formulations are administered intravenously, and are thus formulated in a form suitable for intravenous administration. In another embodiment, the pharmaceutical formulations are administered intraarterially, and are thus formulated in a form suitable for intraarterial administration. In another embodiment, the pharmaceutical formulations are administered intramuscularly, and are thus formulated in a form suitable for intramuscular administration.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other-pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In addition, the formulations may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweetners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

In preparing pharmaceuticals of the present invention, a variety of formulation modifications can be used and manipulated to alter pharmacokinetics and biodistribution. A number of methods for altering pharmacokinetics and biodistribution are known to one of ordinary skill in the art. Examples of such methods include protection of the compositions of the invention in vesicles composed of substances such as proteins, lipids (for example, liposomes, see below), carbohydrates, or synthetic polymers (discussed above). For a general discussion of pharmacokinetics, see, e.g., Remington's, Chapters 37-39.

The ligands of the invention can be delivered alone or as pharmaceutical compositions by any means known in the art, e.g., systemically, regionally, or locally (e.g., directly into, or directed to, a tumor); by intraarterial, intrathecal (IT), intravenous (IV), parenteral, intra-pleural cavity, topical, oral, or local administration, as subcutaneous, intratracheal (e.g., by aerosol) or transmucosal (e.g., buccal, bladder, vaginal, uterine, rectal, nasal mucosa). Actual methods for preparing administrable compositions will be known or apparent to those skilled in the art and are described in detail in the scientific and patent literature, see e.g., Remington's. Parenteral administration is a preferred route of delivery if a high systemic dosage is needed. Actual methods for preparing parenterally administrable compositions will be known or apparent to those skilled in the art and are described in detail, in e.g., Remington's. See also, Bai (1997) *J. Neuroimmunol.* 80:65-75; Warren (1997) *J. Neurol. Sci.* 152:31-38; Tonegawa (1997) *J. Exp. Med.* 186:507-515.

The preparation of pharmaceutical formulations which contain an active component is well understood in the art, for example by mixing, granulating, or tablet-forming processes. The active therapeutic ingredient is often mixed with excipients which are pharmaceutically acceptable and compatible with the active ingredient. For oral administration, the ligands or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the ligands or their physiologically tolerated derivatives such as salts, esters, N-oxides, and the like are converted into a solution, suspension, or emulsion, if desired with the substances customary and suitable for this purpose, for example, solubilizers or other.

An active component can be formulated into the formulation as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicine, salts of the ligands will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic: acid, oxalic acid, citric acid, tartaric acid, carbonic acid or phosphoric acid.

The pharmaceutical compositions of the invention can be administered in a variety of unit dosage forms depending upon the method of administration. Dosages for typical modulatory pharmaceutical compositions are well known to those of skill in the art. Such dosages are typically advisorial in nature and are adjusted depending on the particular therapeutic context, patient tolerance, etc. The amount of ligand adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age, pharmaceutical formulation and concentration of active agent, and the like. In calculating the dosage regimen for a patient, the mode of administration also is taken into consideration. The dosage regimen must also take into consideration the pharmacokinetics, i.e., the pharmaceutical composition's rate of absorption, bioavailability, metabolism, clearance, and the like. See, e.g., the latest Remington's; Egleton (1997) "Bioavailability and transport of peptides and peptide drugs into the brain" Peptides 18:1431-1439; Langer (1990) Science 249:1527-1533.

Yet another aspect of the present invention is directed to a ligand, as hereinbefore defined, which ligand is not IC7.

In one embodiment, said ligand is complexed to a proteinaceous or non-proteinaceous molecule such that the complex is prevented or retarded from crossing the blood brain barrier.

Still another aspect provides a pharmaceutical composition comprising a ligand as hereinbefore defined together with a pharmaceutically acceptable carrier.

In yet another aspect there is provided a ligand as hereinbefore defined for use in therapy.

The present invention is further described by reference to the following non-limiting examples.

Example 1

Figure 3:
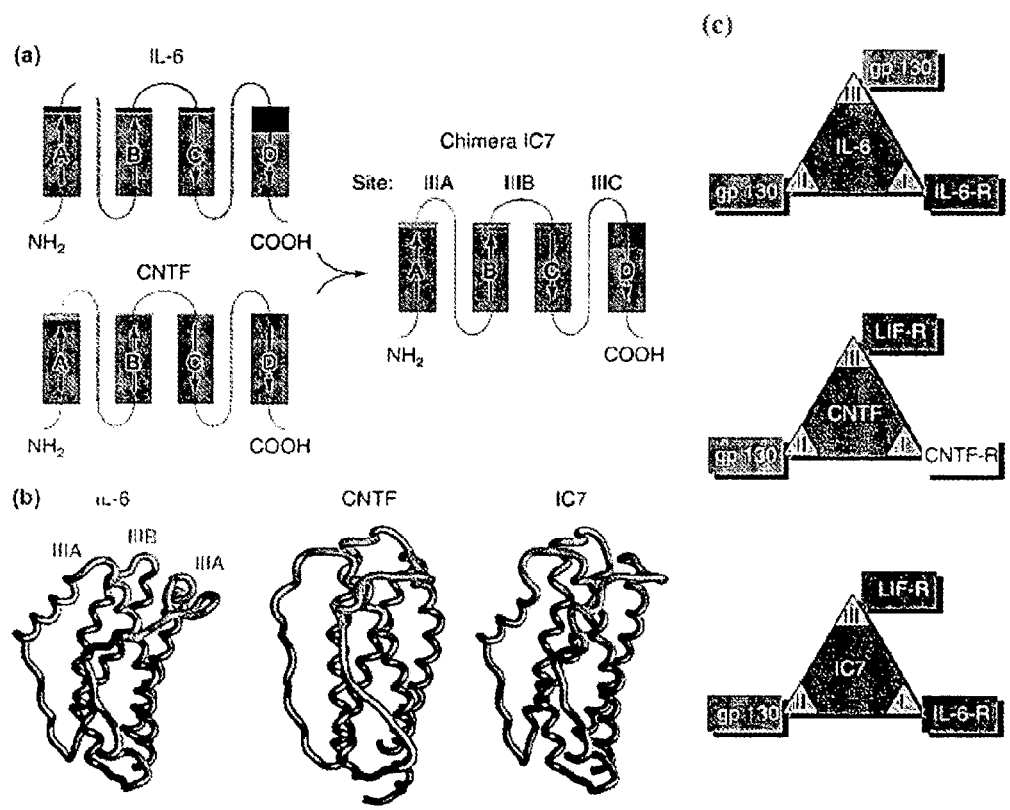
FIG. 3 is (a) an epitope shuffle of receptor-binding sites of IL-6-like cytokines. The figure shows the typical four-helix bundle fold of IL-6, CNTF and IC7, with the characteristic up-up-down-down orientation of the α-helices. Consequently, two long loops (AB_and CD) and one short loop (BC) connect the helices. (b) A ribbon model of IL-6, CNTF IC-7. (c) Receptor requirements of IL-6, CNTF and IC-7.
Figure 4:
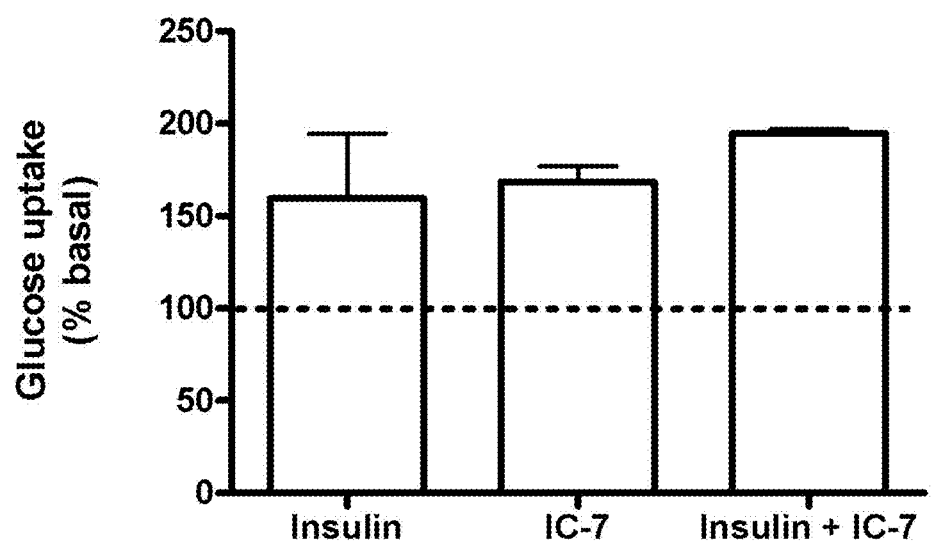
FIG. 4 is a graphical representation depicting that IC-7 stimulates glucose uptake into skeletal muscle. All values are relative to basal glucose uptake, adjusted to 100% (dotted line). Insulin and IC-7 values were derived from three animals, while co-treatment values were derived from two animals.

IC-7 was made in accordance with Kallen et. al. (1999) supra. More specifically IC-7 was developed by substituting the site III loop of IL-6 with the site III loop of CNTF (Kallen et. al., (1999) supra.). The site loop is situated on the C-terminal end of the protein and is the region which binds the either one gp130Rβ or the LIFRβ (FIG. 3).

Example 2

IC-7 Stimulates Glucose Uptake in Soleus Muscle

The soleus muscle was dissected tendon to tendon from anaesthetised C57B1/6 mice and placed immediately into 2 mL of pre-gassed (95% $O_2$, 5% $CO_2$) Krebs-Henseleit buffer and incubated for 10 minutes in a 30° C. water bath with agitation. After 30 minutes of pre-incubation, this buffer was stimulated with insulin, cytokines or a co-treatment of both and incubated for a further 30 minutes. Muscles were then placed into 2 mL of Krebs-Henseleit buffer containing $^3$H-deoxyglucose, $^{14}$C-mannitol and the appropriate stimulus (insulin, cytokine or both) and incubated for 15 mins. Muscles were washed with saline, weighed and processed for determination of the uptake of labelled glucose.

The soleus muscles of C57B1/6 mice were assayed for the effect of insulin, IC-7 and co-treatment of insulin and IC-7 on glucose uptake. As expected, insulin led to 159% increase in skeletal muscle glucose uptake (FIG. 3). IC-7 (100 ng/mL) stimulation led to an equivalent increase in glucose uptake (168%), while co-treatment had a slight synergistic effect (194%).

IC-7 Increases Fatty Acid Oxidation in Skeletal Muscle

The soleus and EDL (extensor digitorum longus) muscles were dissected tendon to tendon from anaesthetised C57B1/6 mice and immediately placed into 2 mL of pre-gassed (95% $O_2$, 5% $CO_2$) Krebs-Henseleit buffer and incubated for 30 minutes in a 30° water bath with agitation. Following this pre-incubation, muscles were transferred into 2 mL of pre-gassed (95% $O_2$, 5% $CO_2$) Krebs-Henseleit buffer containing $^{14}$C-palmitic acid and either IC-7 or vehicle control and incubated for a further 2 hours. Muscles were washed in saline, weighed and processed to quantify any partially oxidized palmitate while the buffer was acidified to release trapped $^{14}CO_2$.

Figure 5:
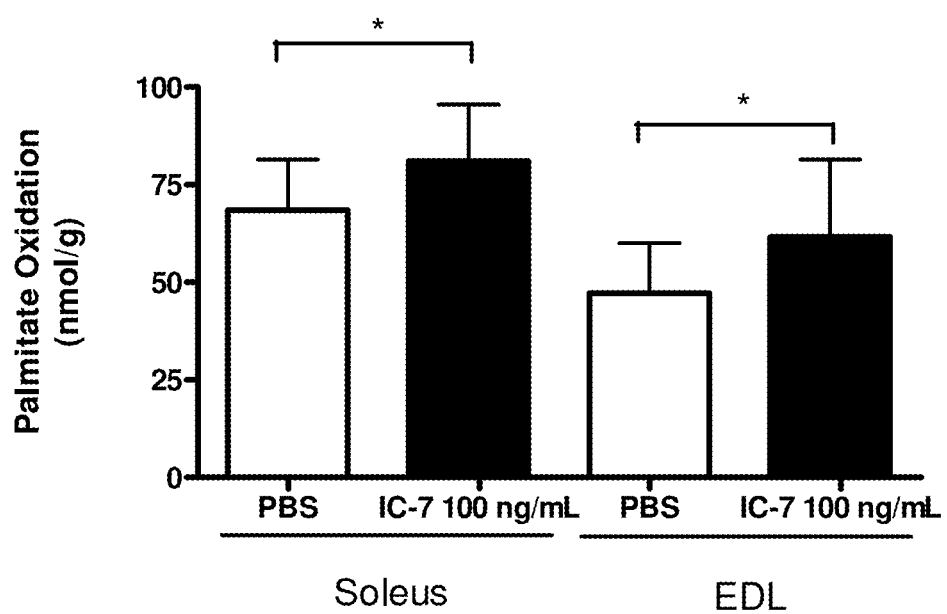
FIG. 5 is a graphical representation depicting that IC-7 increases fatty acid oximation in soleus and EDL muscle (p value=0.005 and 0.034 respectively, n-12).

The soleus and EDL muscles of C57B1/6 mice were assayed for the effect of IC-7 on palmitate oxidation. In both soleus and EDL, 100 ng/mL IC-7 led to a significant increase in the total oxidation of exogenous palmitate (FIG. 5).

Figure 6:
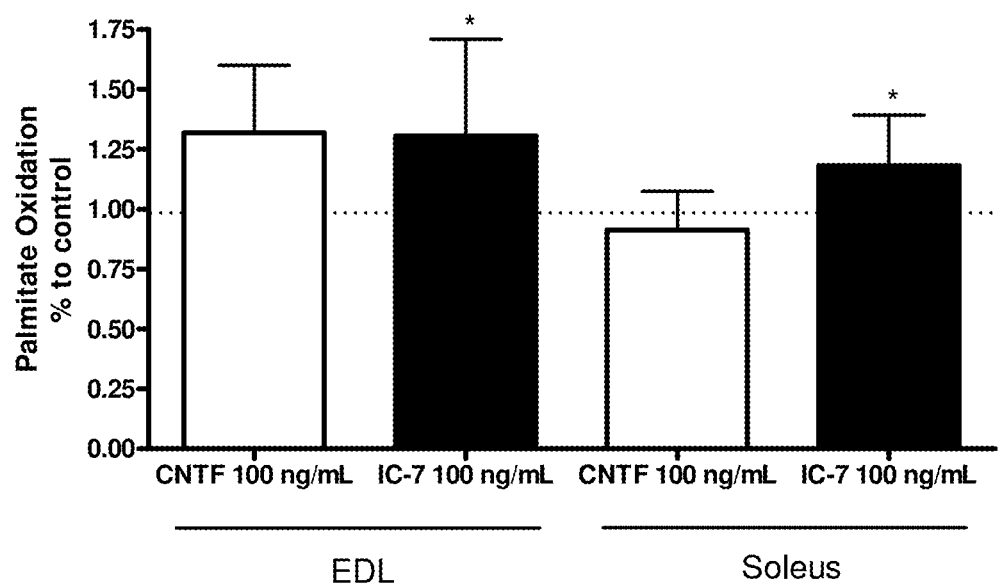
FIG. 6 is a graphical representation depicting that CNTF increases fatty acid oxidation in EDL by not Soleus.

The soleus and EDL muscles of C57B1/6 mice were assayed to compare the effects of IC-7 and CNTF on palmitate oxidation. IC-7 (100 ng/mL) significantly increased exogenous palmitate oxidation in both muscles, while CNTF (100 ng/mL) increased oxidation only in EDL muscles (n=4) (FIG. 6).

Acute Treatment of IC-7 in C57B1/6 Mice

To establish the bioactivity and acute effects of IC-7 in comparison to CNTF on wildtype, chow fed C57B1/6 mice, animals were injected intraperitoneally with vehicle, CNTF (0.3, 0.9 mg/kg), or IC-7 (0.1, 0.3, 0.9 mg/kg). 45 minutes after administration mice were anaesthetised and tissues removed. the phosphorylation of STAT3 was analysed to verify receptor activation.

Figure 7:
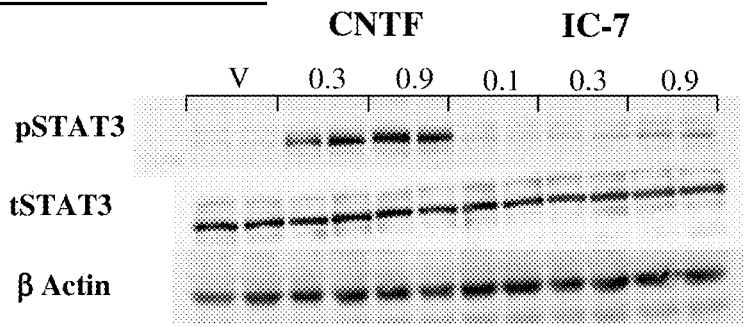
FIG. 7 is an image depicting that IC-7 activates gp130 receptor signalling.
Figure 7:
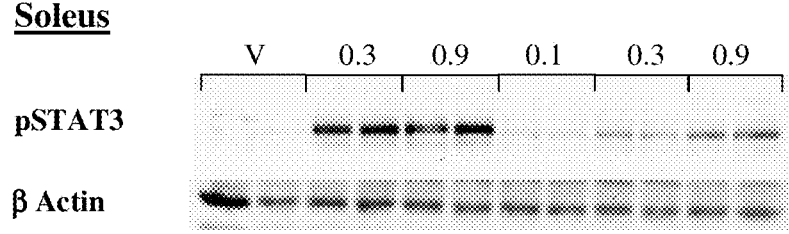
Figure 7:
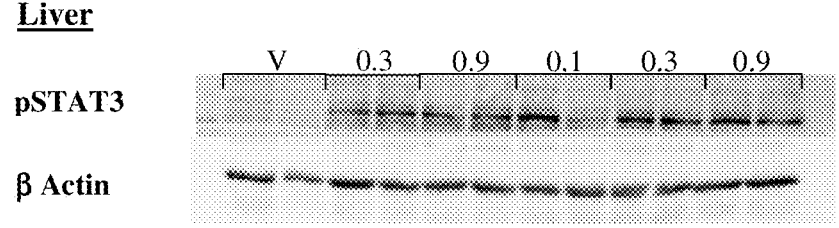
Figure 7:
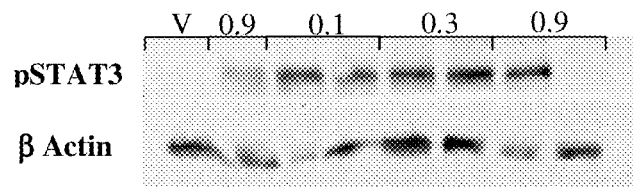
Figure 8:
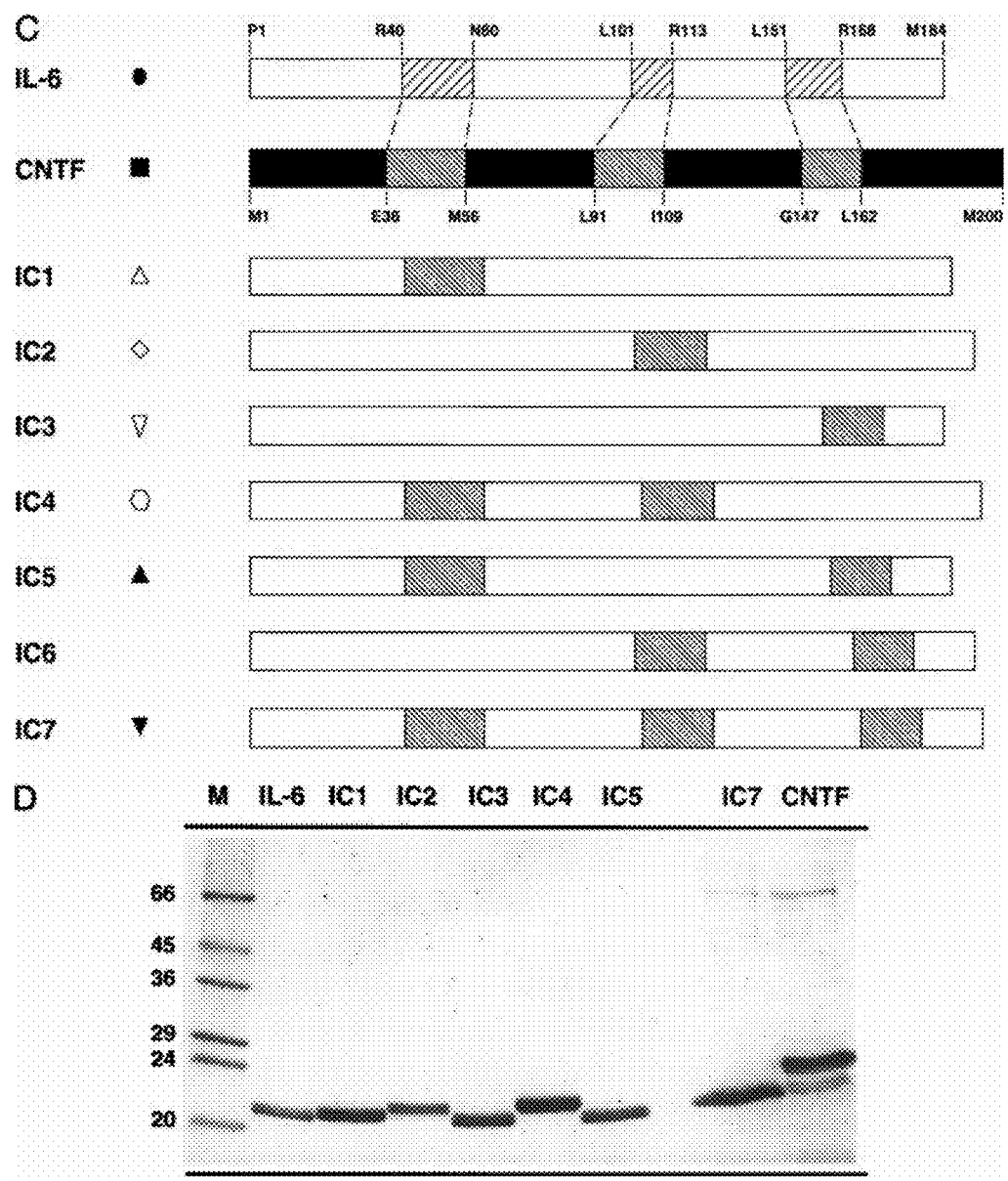
FIG. 8 depicts a bar representation of IL-6, CNTF and the chimeras IC1-IC7. Sequence stretches that are part of the exchanged epitopes of IL-6 and CNTF are hatched. On CNTF the N and C terminal amino acid residues of the transferred stretches are designated in single letter code, on IL-6 the residues adjacent to the transferred CNTF stretches are denoted.
Figure 9:
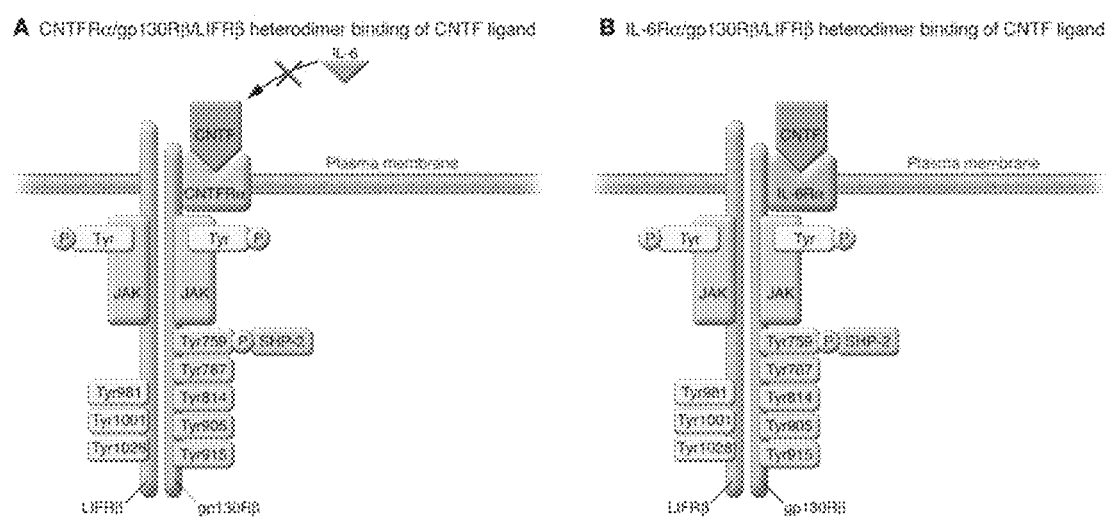
FIG. 9 shows the complex ligand receptor signalling for the 130Rβ cytokine CNTF. In contrast to the mechanism of IL-6Rα/gp130Rβ homodimer binding of IL-6 ligand, CNTF can signal via a heterodimer containing CNTFRα, gp130Rβ and LIFRβ (A) or via a heterodimer containing IL-6Rα, gp130Rβ and LIFRβ (B). While CNTF can signal via IL-6Rα, it cannot do so via a IL-6Rα/130Rβ homodimer as LIF is an absolute requirement.

C57B1/6 mice were i.p injected with vehicle, CNTF (0.3, 0.9 mg/kg) or IC-7 (0.2, 0.3, 0.9 mg/kg) and tissues removed after 45 minutes. The phosphorylation of STAT3, a downstream target of gp130 receptor signalling, was determined as a measure of bioactivity of IC-7 compared to CNTF. In both red gastrocnemius and a soleus muscle CNTF administration led to a robust increase in pSTAT3 (FIG. 7). IC-7 treatment led to a marked, dose-dependent increase in pSTAT3 in skeletal muscle. Both CNTF and IC-7 induced a significant increase in pSTAT3 in liver. In adipose tissue, IC-7 led to a more robust increase in pSTAT3 in comparison to CNTF. These results verify dy that IC-7 is bioactive and capable of activating the gp130 receptor in vivo.

Example 3

Acute Effects of IC-7 on Food Intake, Body Mass and Insulin Sensitivity In Vivo

The data in Example 2 indicates that IC-7 would be a more potent gp130 receptor ligand compared with CNTF. This is most significant because patients in the human trial for Axokine® only developed antibodies on high doses of the peptide (Ettinger et. al. (2003) supra). In previous studies using CNTF, it has been shown that a subcutaneous injection of 0.3 mg/kg was effective in activating AMPK and phosphorylating ACCβ, enhancing fat oxidation and increasing insulin action. Accordingly, these experiments are repeated with the addition of 3 doses of IC-7 (0.05, 0.1 and 0.3 mg/kg). Briefly, male C57/B16 mice (4 weeks of age) mice are placed on a high fat diet for 12 weeks. After this time, conscious mice are injected with the ligands at the aforementioned doses and skeletal muscle and liver are harvested after 45 min. Samples are analysed for activation of AMPK, and phosphorylation of ACCβ, fat oxidation and insulin signalling as outlined in our previous paper. This method will enable the selection of doses of IC-7 for use.

Example 4

Chronic Effects of IC-7 on Food Intake, Body Mass and Insulin Sensitivity In Vivo Male C57/BL6 mice (4 weeks of age) are maintained on either a chow or high fat diet. Mice are fed ad libitum for 12 weeks so as to induce obesity and insulin resistance (in the high fat fed animals). After 11 weeks, animals are injected with CNTF (0.3 mg/kg) or IC-7 or calorically matched and injected with saline every day for the remaining 1 week of the diet. In addition, genetically obese mice (ob/ob) (4 weeks of age) are fed a chow diet for 12 weeks then administered CNTF (0.3 mg/kg), IC-7 or pair fed and given saline via IP injection every day for 1 week. During the 7 d treatment, body weight, energy turnover and activity patterns are monitored. After 7 d of treatment with CNTF or IC-7, animals are sacrificed and fat pads are weighed. Fat oxidation is measured in skeletal muscle and liver as are triacylglycerol, diacylglycerol and ceramide in these tissues. Glucose uptake and insulin signalling are also examined in skeletal muscle.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Altschul et al. (1997) *Nucl. Acids Res.* 25:3389.
Ausubel et al. (1994-1998) Current Protocols in Molecular Biology, John Wiley & Sons Inc., Chapter 15.
Bai (1997) *J. Neuroimmunol.* 80:65-75.
Banga, A. K. (1995) Therapeutic Peptides and Proteins, Formulation, Processing and Delivery Systems, Technomic Publishing Co., Lancaster, Pa.
Bazan, J F (1990a), Haemopoietic receptors and helical cytokines, *Immunol. Today* 11:350-354.
Bazan, J F (1990b), Structural design and molecular evolution of a cytokine receptor superfamily, *Proc. Natl. Acad. Sci.* (USA) 87:6934-6938.
Bazan, J F (1991), Neuropoietic cytokines in the hematopoietic fold, *Neuron* 7:197-208.
Caruthers (1980) *Nucleic Acids Res. Symp. Ser.* 215-223.
Chorev and Goodman (1993) *Acc. Chem. Res.* 26:266-273.
Davis, S et. al. (1991), The receptor for ciliary neurotrophic factor, *Science* 253:59-63.
Davis, S et. al. (1993), LIFR beta and gp130 as heterodimerizing signal transducers of the tripartite CNTF receptor, *Science* 260:1805-1808.
Dobeli (1998) *Protein Expr. Purif.* 12:404-414.

Ettinger, M P, et. al. (2003), Recombinant variant of ciliary neurotrophic factor for weight loss in obese adults: a randomized, dose-ranging study, *JAMA* 289: 1826-1832.

Fix (1996) *Pharm Res.* 13:1760-1764.

Flegal, K M et. al. (1999-2000), Prevalence and trends in obesity among US adults, *JAMA* 288:1723-1727.

Friedman, B et. al. (1992), Regulation of ciliary neurotrophic factor expression in myelin-related Schwann cells in vivo, *Neuron* 9:295-305.

Gallop et al. (1994) *J. Med. Chem.* 37:1233-1251.

Grotzinger, J et. al. (1997) *Proteins Struct. Funct. Genet.* 27:96-109.

Halaas, J L et. al. (1995), Weight-reducing effects of the plasma protein encoded by the obese gene, *Science* 269: 543-546.

Hibi, M et. al. (1990), Molecular cloning and expression of an IL-6 signal transducer, gp130, *Cell* 63:1149-1157.

Hirano, T et. al. (1986), Complementary DNA for a novel human interleukin (BSF-2) that induces B lymphocytes to produce immunoglobulin, *Nature* 324:73-6.

Hogan (1997) *Nature Biotechnology* 15:328-330.

Horn (1980) *Nucleic Acids Res. Symp. Ser.* 225-232.

Ip, N Y et. al. (1993a), The alpha component of the CNTF receptor is required for signalling and defines potential CNTF targets in the adult and during development, *Neuron* 10:89-102.

Ip N Y et. al. (1993b), Injury-induced regulation of ciliary neurotrophic factor mRNA in the adult rat brain, *Eur. J. Neurosci.* 5:25-33.

Kallen, K J et. al. (1999), Receptor recognition sites of cytokines are organized as exchangeable moduls: transfer of the LIFR binding site from CNTF to IL-6, *J. Biol. Chem.* 274:11859-11867.

Kroll (1993) *DNA Cell. Biol.* 12:441-453.

Mascie-Taylor, C G, and Karim, E (2003), The burden of chronic disease, *Science* 302:1921-1922.

Masiakowski, P et. al. (1991), Recombinant human and rat ciliary neurotrophic factors, *J. Neurochem.* 57:1003-1012.

McDonald, J R et. al. (1991), Expression and characterization of recombinant human ciliary neurotrophic factor from *Escherichia coli.*, *Biochim. Biophys. Acta* 1090:70-80.

McDonald et. al. (1995), *EMBO J.* 14:2689-2699.

Merrifield (1997) *Methods Enzymol.* 289:3-13.

Murakami, M et. al. (1993), IL-6-induced homodimerization of gp130 and associated activation of a tyrosine kinase, *Science* 260:1808-1810.

Olson et al. (1993) *J. Med. Chem.* 36:3039-3049.

Padwal, R S, and Majumdar, S R (2007), Drug treatment for obesity: orlistat, sibutramine, and rimonbant, *Lancet* 369: 71-77.

Panayotatos, N et. al. (1995), *J. Biol. Chem.* 270:14007-14014.

Patton (1998) *Biotechniques* 16:141-143.

Putney (1998) *Nat. Biotechnol.* 16:153-157.

Remington's Pharmaceutical Science, Mack Publishing Company, Easton, Pa.

Rende, M et. al. (1992), Immunolocalization of ciliary neuroneotrophic factor in adult rat sciatic nerve, *Glia* 5:25-32.

Roberge (1995) *Science* 269:202.

Rudge, J S et. al. (1992), Expression of ciliary neurotrophic factor and the neurotrophins—nerve growth factor brain-derived neurotrophic factor and neurotrophin-3—in cultured rat hippocampal astrocytes, *Eur. J. Neurosci.* 4:459-471.

Samanen (1996) *J. Pharm. Pharmacol.* 48:119-135.

Sayani (1996) Systemic delivery of peptides and proteins across absorptive mucosae, *Crit. Rev, Ther. Drug Carrier Syst.* 13:85-184.

Sendtner, M et. al. (1992a), Synthesis and localization of ciliary neurotrophic factor in the sciatic nerve of the adult rat after lesion and during regeneration, *J. Cell Biol* 118:139-148.

Simpson, R J et. al. (1988), Characterization of a recombinant murine interleukin-6: assignment of disulphide bonds, *Biochem. Biophys. Res. Commun.* 157:364-372.

Stahl, N et. al. (1993), Cross-linking identifies leukaemia inhibitory factor-binding protein as a ciliary neurotrophic factor receptor component, *J. Biol. Chem.* 268:7628-7631.

Taga, T and Kishimoto, T (1992), Cytokine receptors and signal transduction, *FASEB J.* 6:3387-3396.

Taga, T et. al. (1989), Interleukin-6 triggers the association of its receptor with a possible signal transducer, gp130, *Cell* 58:573-581.

Tartaglia, L A et. al. (1995), Identification and expression cloning of a leptin receptor, OB-R, *Cell* 83:1263-1271.

Tonegawa (1997) *J. Exp. Med.* 186:507-515.

U.S. Pat. No. 5,391,377.

Van Heek, M et. al. (1997) Diet-induced obese mice develop peripheral, but not central, resistance to leptin, *J. Clin. Invest.* 99:385-390.

Warren (1997) *J. Neurol. Sci.* 152:31-38.

Williams (1995) *Biochemistry* 34:1787-1797.

Yamasaki, K et. al. (1988), Cloning and expression of the human interleukin-6 (BSF-2/IFN beta 2) receptor, *Science* 241:825-828.

Yin, T et. al. (1993), Involvement of IL-6 signal transducer gp130 in IL-11 mediated signal transduction, *J. Immunol.* 151: 2555-2561.

Zhang, Y et. al. (1994), Positional cloning of the mouse obese gene and its human homologue, *Nature* 372:425-432.

The claims defining the invention are as follows:

1. A method for increasing fat oxidation wherein the method comprises administering to the mammal a polypeptide comprising the amino acid sequence set forth in SEQ ID NO: 7, which amino acid sequence corresponds to the amino acid sequence of an IL-6/CNTF chimeric polypeptide in which the site III loop of the CNTF replaces the site III loop of IL-6 and which comprises an IL-6 receptor binding site, a gp130 binding site and a LIF receptor binding site that permit the polypeptide to bind the IL-6 receptor and to signal via a gp130/LIF receptor heterodimer.

2. The method according to claim 1, wherein the mammal is obese and has a condition selected from the group consisting of osteoarthritis, type II diabetes mellitus, hypertension, stroke, and cardiovascular disease.

3. The method of claim 1, wherein the mammal is a human.

* * * * *

UNITED STATES PATENT AND TRADEMARK OFFICE
CERTIFICATE OF CORRECTION

PATENT NO. : 9,765,129 B2
APPLICATION NO. : 13/968977
DATED : September 19, 2017
INVENTOR(S) : Mark Anthony Febbraio It is certified that error appears in the above-identified patent and that said Letters Patent is hereby corrected as shown below:

In the Specification

In Column 2 at Lines 20-21, Change "rimonbant," to --rimonabant,--.

In Column 4 at Line 44, Change "moduls:" to --modules:--.

In Column 5 at Line 43, Change "anther" to --another--.

In Column 6 at Line 29, Change "130Rβ" to --gp130Rβ--.

In Column 6 at Line 34, Change "IL-6Rα/130Rβ" to --IL-6Rα/gp130Rβ--.

In Column 7 at Line 40, Change "130"" to --"gp130"--.

In Column 8 at Line 60, Change "(3" to --β--.

In Column 9 at Line 58, Change "neuroneotrophic" to --neuronotrophic--.

In Columns 13-14 at Line 50 (approx.), Change "L-N-methylisolleucine" to --L-N-methylisoleucine--.

In Columns 15-16 at Line 7 (approx.), Change "α-methylcylcopentylalanine" to --α methylcyclopentylalanine--.

In Columns 15-16 at Line 8 (approx.), Change "α-methyl-α-napthylalanine" to --α-methyl-α naphthylalanine--.

In Columns 15-16 at Line 14 (approx.), Change "α-napthylalanine" to --α-naphthylalanine--.

Signed and Sealed this
Third Day of April, 2018

Andrei Iancu
*Director of the United States Patent and Trademark Office*

CERTIFICATE OF CORRECTION (continued)
U.S. Pat. No. 9,765,129 B2

In Columns 15-16 at Line 24 (approx.), Change "N-cylcododecylglycine" to --N-cyclododecylglycine--.

In Columns 15-16 at Line 34 (approx.), Change "N-(3-indolylyethyl)glycine" to --N-(3 indolylethyl)glycine--.

In Columns 15-16 at Line 43 (approx.), Change "N-methyla-napthylalanine" to --N-methyl-α naphthylalanine--.

In Column 21 at Line 21, Change "respiratorally," to --respiratorily,--.

In Column 21 at Line 23, Change "intraoccularly," to --intraocularly,--.

In Column 21 at Line 24, Change "intracereberally," to --intracerebrally,--.

In Column 21 at Lines 51-52, Change "croscarmelose" to --croscarmellose--.

In Column 24 at Line 53, Change "Tris-HCI," to --Tris-HCl,--.

In Column 24 at Line 61, Change "hyroxypropylmethyl" to --hydroxypropylmethyl--.

In Column 24 at Line 63, Change "sweetners" to --sweeteners--.

In Column 28 at Line 67, Change "Purif:" to --Purif.--.

In Column 29 at Line 31 (approx.), Change "moduls:" to --modules:--.

In Column 29 at Line 51 (approx.), Change "rimonbant," to --rimonabant,--.

In Column 30 at Line 8 (approx.), Change "neuroneotrophic" to --neuronotrophic--.

SEQUENCE LISTING

```
<160> NUMBER OF SEQ ID NOS: 7

<210> SEQ ID NO 1
<211> LENGTH: 212
<212> TYPE: PRT
<213> ORGANISM: Homo sapiens
<220> FEATURE:
<221> NAME/KEY: POLYPEPTIDE
<222> LOCATION: (1)..(212)
<223> OTHER INFORMATION: Full-length IL-6 with signal sequence
```

<400> SEQUENCE: 1

```
Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210
```

<210> SEQ ID NO 2
<211> LENGTH: 184
<212> TYPE: PRT
<213> ORGANISM: Homo sapiens
<220> FEATURE:
<221> NAME/KEY: POLYPEPTIDE
<222> LOCATION: (1)..(184)
<223> OTHER INFORMATION: Mature IL-6 without signal sequence

<400> SEQUENCE: 2

```
Pro Val Pro Pro Gly Glu Asp Ser Lys Asp Val Ala Ala Pro His Arg
1               5                   10                  15

Gln Pro Leu Thr Ser Ser Glu Arg Ile Asp Lys Gln Ile Arg Tyr Ile
            20                  25                  30

Leu Asp Gly Ile Ser Ala Leu Arg Lys Glu Thr Cys Asn Lys Ser Asn
        35                  40                  45

Met Cys Glu Ser Ser Lys Glu Ala Leu Ala Glu Asn Asn Leu Asn Leu
    50                  55                  60

Pro Lys Met Ala Glu Lys Asp Gly Cys Phe Gln Ser Gly Phe Asn Glu
65                  70                  75                  80

Glu Thr Cys Leu Val Lys Ile Ile Thr Gly Leu Leu Glu Phe Glu Val
                85                  90                  95

Tyr Leu Glu Tyr Leu Gln Asn Arg Phe Glu Ser Ser Glu Glu Gln Ala
            100                 105                 110

Arg Ala Val Gln Met Ser Thr Lys Val Leu Ile Gln Phe Leu Gln Lys
        115                 120                 125
```

-continued

Lys Ala Lys Asn Leu Asp Ala Ile Thr Thr Pro Asp Pro Thr Thr Asn
    130                 135                 140

Ala Ser Leu Leu Thr Lys Leu Gln Ala Gln Asn Gln Trp Leu Gln Asp
145                 150                 155                 160

Met Thr Thr His Leu Ile Leu Arg Ser Phe Lys Glu Phe Leu Gln Ser
                165                 170                 175

Ser Leu Arg Ala Leu Arg Gln Met
            180

<210> SEQ ID NO 3
<211> LENGTH: 200
<212> TYPE: PRT
<213> ORGANISM: Homo sapiens
<220> FEATURE:
<221> NAME/KEY: POLYPEPTIDE
<222> LOCATION: (1)..(200)
<223> OTHER INFORMATION: CNTF

<400> SEQUENCE: 3

Met Ala Phe Thr Glu His Ser Pro Leu Thr Pro His Arg Arg Asp Leu
1               5                   10                  15

Cys Ser Arg Ser Ile Trp Leu Ala Arg Lys Ile Arg Ser Asp Leu Thr
            20                  25                  30

Ala Leu Thr Glu Ser Tyr Val Lys His Gln Gly Leu Asn Lys Asn Ile
        35                  40                  45

Asn Leu Asp Ser Ala Asp Gly Met Pro Val Ala Ser Thr Asp Gln Trp
    50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
        195                 200

<210> SEQ ID NO 4
<211> LENGTH: 21
<212> TYPE: PRT
<213> ORGANISM: Homo sapiens
<220> FEATURE:
<221> NAME/KEY: PEPTIDE
<222> LOCATION: (1)..(21)
<223> OTHER INFORMATION: CNTF peptide Glu36-Met56

```
<400> SEQUENCE: 4

Glu Ser Tyr Val Lys His Gln Gly Leu Asn Lys Asn Ile Asn Leu Asp
1               5                   10                  15

Ser Ala Asp Gly Met
            20

<210> SEQ ID NO 5
<211> LENGTH: 19
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: CNTF peptide Leu91-Ile109

<400> SEQUENCE: 5

Leu Glu Asp Gln Gln Val His Phe Thr Pro Thr Glu Gly Asp Phe His
1               5                   10                  15

Gln Ala Ile

<210> SEQ ID NO 6
<211> LENGTH: 16
<212> TYPE: PRT
<213> ORGANISM: Homo sapiens
<220> FEATURE:
<221> NAME/KEY: PEPTIDE
<222> LOCATION: (1)..(16)
<223> OTHER INFORMATION: CNTF peptide Gly147-Leu162

<400> SEQUENCE: 6

Gly Asp Gly Gly Leu Phe Glu Lys Lys Leu Trp Gly Leu Lys Val Leu
1               5                   10                  15

<210> SEQ ID NO 7
<211> LENGTH: 196
<212> TYPE: PRT
<213> ORGANISM: Artificial
<220> FEATURE:
<223> OTHER INFORMATION: Recombinant IC7

<400> SEQUENCE: 7

Met Ala Pro Val Pro Pro Gly Glu Asp Ser Lys Asp Val Ala Ala Pro
1               5                   10                  15

His Arg Gln Pro Leu Thr Ser Ser Glu Arg Ile Asp Lys Gln Ile Arg
                20                  25                  30

Tyr Ile Leu Asp Gly Ile Ser Ala Leu Arg Glu Ser Tyr Val Lys His
            35                  40                  45

Gln Gly Leu Asn Lys Asn Ile Asn Leu Asp Ser Ala Asp Gly Met Asn
        50                  55                  60

Asn Leu Asn Leu Pro Lys Met Ala Glu Lys Asp Gly Cys Phe Gln Ser
65                  70                  75                  80

Gly Phe Asn Glu Glu Thr Cys Leu Val Lys Ile Ile Thr Gly Leu Leu
                85                  90                  95

Glu Phe Glu Val Tyr Leu Glu Tyr Leu Leu Glu Asp Gln Gln Val His
            100                 105                 110

Phe Thr Pro Thr Glu Gly Asp Phe His Gln Ala Ile Arg Ala Val Gln
        115                 120                 125

Met Ser Thr Lys Val Leu Ile Gln Phe Leu Gln Lys Lys Ala Lys Asn
    130                 135                 140

Leu Asp Ala Ile Thr Thr Pro Asp Pro Thr Thr Asn Ala Ser Leu Leu
145                 150                 155                 160
```

-continued

```
Thr Lys Leu Gly Asp Gly Gly Leu Phe Glu Lys Lys Leu Trp Gly Leu
                165                 170                 175

Lys Val Leu Arg Ser Phe Lys Glu Phe Leu Gln Ser Ser Leu Arg Ala
                180                 185                 190

Leu Arg Gln Met
        195
```